US011060996B2

(12) United States Patent
Nakagaki et al.

(10) Patent No.: US 11,060,996 B2
(45) Date of Patent: Jul. 13, 2021

(54) GAS SENSOR, AND METHOD FOR MEASURING CONCENTRATIONS OF PLURALITY OF TARGET COMPONENTS IN GAS TO BE MEASURED

(71) Applicant: NGK INSULATORS, LTD., Nagoya (JP)

(72) Inventors: Kunihiko Nakagaki, Kronberg im Taunus (DE); Dietmar Schmitt, Kronberg im Taunus (DE)

(73) Assignee: NGK INSULATORS, LTD., Nagoya (JP)

(*) Notice: Subject to any disclaimer, the term of this patent is extended or adjusted under 35 U.S.C. 154(b) by 185 days.

(21) Appl. No.: 16/228,827

(22) Filed: Dec. 21, 2018

(65) Prior Publication Data

US 2019/0137441 A1 May 9, 2019

Related U.S. Application Data

(63) Continuation of application No. PCT/JP2017/022945, filed on Jun. 22, 2017.

(30) Foreign Application Priority Data

Jun. 23, 2016 (JP) .............................. JP2016-124420

(51) Int. Cl.
*G01N 27/407* (2006.01)
*G01N 27/416* (2006.01)
(Continued)

(52) U.S. Cl.
CPC ....... *G01N 27/4071* (2013.01); *G01N 27/409* (2013.01); *G01N 27/4074* (2013.01);
(Continued)

(58) Field of Classification Search
CPC .. G01N 27/41; G01N 27/407; G01N 33/0037; G01N 33/0054; F01N 2560/021; F01N 2560/026
See application file for complete search history.

(56) References Cited

U.S. PATENT DOCUMENTS 6,083,176 A * 7/2000 Terwilliger ........ A61B 10/0233
600/562
2005/0210657 A1* 9/2005 Nakagaki ............. G01N 27/419
29/592.1
(Continued)

FOREIGN PATENT DOCUMENTS

JP 2009-511859 A 3/2009
JP 2009-243942 A 10/2009
(Continued)

OTHER PUBLICATIONS

JPO computer-generated English langauge trasnlation of the Description section of Japanese patent application JP 2014-136914, which published as JP 2016-14597A, downloaded Nov. 30, 2020. (Year: 2014).*
(Continued)

*Primary Examiner* — Alexander S Noguerola
(74) *Attorney, Agent, or Firm* — Mattingly & Malur, PC

(57) ABSTRACT

A gas sensor, and a method for measuring the concentrations of a plurality of target components in a gas to be measured are disclosed. The gas sensor is provided with: an oxygen concentration control means for controlling the oxygen concentration in an oxygen concentration adjustment chamber; a temperature control means for controlling the temperature of a sensor element; a condition setting means which sets the oxygen concentration of the oxygen concentration adjustment chamber and/or the temperature of the sensor element to conditions corresponding to the types of target components in the introduced gas to be measured; and
(Continued)

a concentration calculation means which calculates the concentrations of the different target components on the basis of the respective sensor outputs obtained under the plurality of conditions corresponding to the types of target components.

12 Claims, 23 Drawing Sheets

(51) Int. Cl.
    *G01N 33/00* (2006.01)
    *G01N 27/409* (2006.01)
    *G01N 27/417* (2006.01)

(52) U.S. Cl.
    CPC ......... *G01N 27/416* (2013.01); *G01N 27/417* (2013.01); *G01N 33/0037* (2013.01); *G01N 33/0054* (2013.01); *F01N 2560/021* (2013.01); *F01N 2560/026* (2013.01)

(56) References Cited

U.S. PATENT DOCUMENTS

| | | | |
|---|---|---|---|
| 2007/0080074 | A1 | 4/2007 | Wang et al. |
| 2007/0080075 | A1* | 4/2007 | Wang ................. G01N 33/0037 205/781 |
| 2015/0276659 | A1 | 10/2015 | Sekiya et al. |

FOREIGN PATENT DOCUMENTS

| | | |
|---|---|---|
| JP | 2013-068632 A | 4/2013 |
| JP | 2014-139579 A | 7/2014 |
| JP | 2015-200643 A | 11/2015 |
| JP | 2016-014597 A | 1/2016 |

OTHER PUBLICATIONS

Chinese Office Action issued in corresponding Chinese Patent Application No. 201780038692.0 dated Aug. 4, 2020.
International Search Report of PCT/JP2017/022945 dated Aug. 29, 2017.

* cited by examiner

FIG. 9

| TWO COMPONENT SYSTEM CONCENTRATIONS (ppm) | | | SENSOR OUTPUT (μA) UNDER 1ST CONDITION | | | SENSOR OUTPUT (μA) UNDER 2ND CONDITION | | | OUTPUT DIFFERENCE (μA) | POINT |
|---|---|---|---|---|---|---|---|---|---|---|
| Total | NO | NO₂ | Total | NO | NO₂ | Total | NO | NO₂ | #2-#1 | |
| 500 ppm SYSTEM | | | | | | | | | | |
| 500 | 500 | 0 | 2.505 | 2.505 | 0.000 | 2.550 | 2.500 | 0.000 | 0.045 | p1 |
| 511 | 400 | 111 | 2.505 | 2.000 | 0.500 | 2.672 | 2.000 | 0.622 | 0.167 | p2 |
| 522 | 300 | 222 | 2.505 | 1.500 | 1.000 | 2.794 | 1.500 | 1.244 | 0.289 | p3 |
| 533 | 200 | 333 | 2.505 | 1.000 | 1.500 | 2.916 | 1.000 | 1.866 | 0.411 | p4 |
| 544 | 100 | 444 | 2.505 | 0.500 | 2.000 | 3.039 | 0.500 | 2.489 | 0.534 | p5 |
| 550 | 50 | 500 | 2.505 | 0.250 | 2.250 | 3.100 | 0.250 | 2.800 | 0.595 | p6 |
| 556 | 0 | 556 | 2.505 | 0.000 | 2.500 | 3.161 | 0.000 | 3.111 | 0.656 | p7 |
| 250 ppm SYSTEM | | | | | | | | | | |
| 250 | 250 | 0 | 1.255 | 1.250 | 0.000 | 1.300 | 1.250 | 0.000 | 0.045 | p8 |
| 256 | 200 | 56 | 1.255 | 1.000 | 0.250 | 1.361 | 1.000 | 0.311 | 0.106 | p9 |
| 261 | 150 | 111 | 1.255 | 0.750 | 0.500 | 1.422 | 0.750 | 0.622 | 0.167 | p10 |
| 267 | 100 | 167 | 1.255 | 0.500 | 0.750 | 1.483 | 0.500 | 0.933 | 0.228 | p11 |
| 272 | 50 | 222 | 1.255 | 0.250 | 1.000 | 1.544 | 0.250 | 1.244 | 0.289 | p12 |
| 278 | 0 | 278 | 1.255 | 0.000 | 1.250 | 1.605 | 0.000 | 1.555 | 0.350 | p13 |
| 125 ppm SYSTEM | | | | | | | | | | |
| 125 | 125 | 0 | 0.630 | 0.625 | 0.000 | 0.675 | 0.625 | 0.000 | 0.045 | p14 |
| 128 | 100 | 28 | 0.630 | 0.500 | 0.125 | 0.705 | 0.500 | 0.155 | 0.075 | p15 |
| 131 | 75 | 56 | 0.630 | 0.375 | 0.250 | 0.736 | 0.375 | 0.311 | 0.106 | p16 |
| 133 | 50 | 83 | 0.630 | 0.250 | 0.375 | 0.766 | 0.250 | 0.466 | 0.136 | p17 |
| 136 | 25 | 111 | 0.630 | 0.125 | 0.500 | 0.797 | 0.125 | 0.622 | 0.167 | p18 |
| 139 | 0 | 139 | 0.630 | 0.000 | 0.625 | 0.827 | 0.000 | 0.777 | 0.197 | p19 |
| 0 ppm SYSTEM | | | | | | | | | | |
| 0 | 0 | 0 | 0.005 | 0.000 | 0.000 | 0.050 | 0.000 | 0.000 | 0.045 | p20 |

FIG. 20

500 ppm SYSTEM

| CONCENTRATIONS (ppm) | | | SENSOR OUTPUT (μA) UNDER 1ST CONDITION | | | | SENSOR OUTPUT (μA) UNDER 2ND CONDITION | | | | OUTPUT DIFFERENCE (μA) | SENSOR OUTPUT (μA) UNDER 3RD CONDITION | | | | OUTPUT DIFFERENCE (μA) | POINT |
|---|---|---|---|---|---|---|---|---|---|---|---|---|---|---|---|---|---|
| Total | NO | NO$_2$ | NH$_3$ | Total | NO | NO$_2$ | NH$_3$ | Total | NO | NO$_2$ | NH$_3$ | #2-#1 | Total | NO | NO$_2$ | NH$_3$ | #3-#2 | |
| 500 | 500 | 0 | 0 | 2.505 | 2.500 | 0.000 | 0.000 | 2.55 | 2.500 | 0.000 | 0.000 | 0.045 | 2.251 | 2.250 | 0.000 | 0.000 | 0.299 | p1 |
| 491 | 400 | 0 | 91 | 2.505 | 2.000 | 0.000 | 0.500 | 2.55 | 2.000 | 0.000 | 0.500 | 0.045 | 2.128 | 1.800 | 0.000 | 0.327 | 0.422 | p2 |
| 482 | 300 | 0 | 182 | 2.505 | 1.500 | 0.000 | 1.000 | 2.55 | 1.500 | 0.000 | 1.000 | 0.045 | 2.006 | 1.350 | 0.000 | 0.655 | 0.544 | p3 |
| 473 | 200 | 0 | 273 | 2.505 | 1.000 | 0.000 | 1.500 | 2.55 | 1.000 | 0.000 | 1.500 | 0.045 | 1.883 | 0.900 | 0.000 | 0.982 | 0.667 | p4 |
| 464 | 100 | 0 | 364 | 2.505 | 0.500 | 0.000 | 2.000 | 2.55 | 0.500 | 0.000 | 2.000 | 0.045 | 1.760 | 0.450 | 0.000 | 1.309 | 0.790 | p5 |
| 459 | 50 | 0 | 409 | 2.505 | 0.250 | 0.000 | 2.250 | 2.55 | 0.250 | 0.000 | 2.250 | 0.045 | 1.698 | 0.225 | 0.000 | 1.472 | 0.852 | p6 |
| 455 | 0 | 0 | 455 | 2.505 | 0.000 | 0.000 | 2.500 | 2.55 | 0.000 | 0.000 | 2.500 | 0.045 | 1.637 | 0.000 | 0.000 | 1.636 | 0.913 | p7 |
| 500 | 500 | 0 | 0 | 2.505 | 2.500 | 0.000 | 0.000 | 2.55 | 2.500 | 0.000 | 0.000 | 0.045 | 2.251 | 2.250 | 0.000 | 0.000 | 0.299 | p8 |
| 511 | 400 | 111 | 0 | 2.505 | 2.000 | 0.500 | 0.000 | 2.67 | 2.000 | 0.622 | 0.000 | 0.165 | 2.245 | 1.800 | 0.444 | 0.000 | 0.425 | p9 |
| 522 | 300 | 222 | 0 | 2.505 | 1.500 | 1.000 | 0.000 | 2.79 | 1.500 | 1.244 | 0.000 | 0.285 | 2.240 | 1.350 | 0.889 | 0.000 | 0.550 | p10 |
| 533 | 200 | 333 | 0 | 2.505 | 1.000 | 1.500 | 0.000 | 2.92 | 1.000 | 1.866 | 0.000 | 0.415 | 2.234 | 0.900 | 1.333 | 0.000 | 0.686 | p11 |
| 544 | 100 | 444 | 0 | 2.505 | 0.500 | 2.000 | 0.000 | 3.04 | 0.500 | 2.489 | 0.000 | 0.535 | 2.229 | 0.450 | 1.778 | 0.000 | 0.811 | p12 |
| 550 | 50 | 500 | 0 | 2.505 | 0.250 | 2.250 | 0.000 | 3.10 | 0.250 | 2.800 | 0.000 | 0.595 | 2.226 | 0.225 | 2.000 | 0.000 | 0.874 | p13 |
| 556 | 0 | 556 | 0 | 2.505 | 0.000 | 2.500 | 0.000 | 3.16 | 0.000 | 3.111 | 0.000 | 0.655 | 2.223 | 0.000 | 2.222 | 0.000 | 0.937 | p14 |
| 500 | 500 | 0 | 0 | 2.505 | 2.500 | 0.000 | 0.000 | 2.55 | 2.500 | 0.000 | 0.000 | 0.045 | 2.251 | 2.250 | 0.000 | 0.000 | 0.299 | p15 |
| 500 | 400 | 50 | 50 | 2.505 | 2.000 | 0.225 | 0.275 | 2.61 | 2.000 | 0.280 | 0.275 | 0.105 | 2.181 | 1.800 | 0.200 | 0.180 | 0.429 | p16 |
| 500 | 300 | 100 | 100 | 2.505 | 1.500 | 0.450 | 0.550 | 2.66 | 1.500 | 0.560 | 0.550 | 0.155 | 2.111 | 1.350 | 0.400 | 0.360 | 0.549 | p17 |
| 500 | 200 | 150 | 150 | 2.505 | 1.000 | 0.675 | 0.825 | 2.72 | 1.000 | 0.840 | 0.825 | 0.215 | 2.041 | 0.900 | 0.600 | 0.540 | 0.679 | p18 |
| 500 | 100 | 200 | 200 | 2.505 | 0.500 | 0.900 | 1.100 | 2.77 | 0.500 | 1.120 | 1.100 | 0.265 | 1.971 | 0.450 | 0.800 | 0.720 | 0.799 | p19 |
| 509 | 0 | 300 | 209 | 2.505 | 0.000 | 1.350 | 1.150 | 2.88 | 0.250 | 1.680 | 1.150 | 0.375 | 1.953 | 0.000 | 1.200 | 0.752 | 0.927 | p20 |
| 528 | 0 | 400 | 128 | 2.505 | 0.000 | 1.800 | 0.701 | 2.99 | 0.000 | 2.240 | 0.700 | 0.485 | 2.059 | 0.000 | 1.600 | 0.458 | 0.931 | p21 |
| 546 | 0 | 500 | 46 | 2.505 | 0.000 | 2.250 | 0.250 | 3.10 | 0.000 | 2.800 | 0.250 | 0.595 | 2.165 | 0.000 | 2.000 | 0.164 | 0.935 | p22 |

GAS SENSOR, AND METHOD FOR MEASURING CONCENTRATIONS OF PLURALITY OF TARGET COMPONENTS IN GAS TO BE MEASURED

CROSS-REFERENCE TO RELATED APPLICATIONS

This application is a Continuation of International Application No. PCT/JP2017/022945 filed on Jun. 22, 2017, which is based upon and claims the benefit of priority from Japanese Patent Application No. 2016-124420 filed on Jun. 23, 2016, the contents all of which are incorporated herein by reference.

TECHNICAL FIELD

The present invention relates to a gas sensor, which is capable of measuring respective concentrations of a plurality of target components in a gas to be measured, as well as to a method of measuring concentrations of a plurality of target components in a gas to be measured.

BACKGROUND ART

Conventionally, an NOx sensor (a serially arranged two-chamber type NOx sensor) having a serially arranged two-chamber structure, and a NOx measurement method using the same (for example, refer to Japanese Laid-Open Patent Publication No. 2015-200643), and a mixed potential type, or a variable resistance type $NO_2$ sensor in which an oxide semiconductor electrode is used, or an $NH_3$ sensor are known (for example, refer to Japanese Laid-Open Patent Publication No. 2013-068632 and Japanese Laid-Open Patent Publication No. 2009-243942).

Further, a method of measuring an $NH_3$ concentration using a mixed potential of an oxide semiconductor electrode is known. This method is a method in which the NOx concentration is measured by another sensor, and in the case that NO, $NO_2$ are not present, the mixed potential of the oxide semiconductor electrode is used as is, whereas, in the case that NO, $NO_2$ are present, the mixed potential of the oxide semiconductor electrode is corrected (see, for example, Japanese Laid-Open Patent Publication No. 2009-511859 (PCT)).

SUMMARY OF INVENTION

In recent years, there is a tendency for regulations in regard to $CO_2$ emission levels to be strengthened, and the adoption rate of diesel vehicles is increasing in respective countries. Diesel engines using lean combustion possess a disadvantage in that it is difficult to purify NOx in exhaust gas that contains an excessive amount of oxygen instead of a small amount of $CO_2$ emissions. For this reason, similar to strengthening regulations concerning $CO_2$ emissions, regulations concerning NOx emissions are also being strengthened. Currently, a selective reduction type catalyst system (hereinafter referred to as an SCR system) which can perform NOx purification without impairing $CO_2$ emission, that is, without a loss in fuel consumption, occupies the mainstream of NOx purification. In such an SCR system, injected urea is reacted with exhaust gas to produce ammonia, and the ammonia and NOx are reacted and are thereby decomposed into $N_2$ and $O_2$. In the SCR system, in order that the NOx purification efficiency is made close to 100%, it is necessary to increase the injected amount of urea. However, if the injected amount of urea is increased, unreacted ammonia may be discharged into the atmosphere. Therefore, a sensor capable of distinguishing between NOx and ammonia is required.

Furthermore, in the United States, preparations are being advanced with respect to obligations for individual failure diagnosis of oxidation catalysts (hereinafter referred to as DOC catalysts), diesel particulate filters (hereinafter referred to as DPF), and selective reduction type catalysts (hereinafter referred to as SCR catalysts). Although failure diagnosis of DPF and SCR catalysts are possible with existing PM sensors and NOx sensors, an effective failure diagnosis technique has not been discovered with respect to DOC catalysts. Currently, a method of measuring an amount of hydrocarbons (hereinafter referred to as HC) leaking downstream from a DOC catalyst at a low temperature of 200° C. or less, and a method of judging a failure from a ratio of NO and $NO_2$ that are discharged downstream from a DOC catalyst are recommended. In particular, in the ratio of NO and $NO_2$, since a reduction in $NO_2$ occurs earlier than an increase in the HC outflow amount, such a method is expected to be a safer method of fault diagnosis. For this purpose, a sensor that is capable of distinguishing between NO and $NO_2$ is demanded.

In the NOx sensor and the NOx measurement method described in the aforementioned Japanese Laid-Open Patent Publication No. 2015-200643, NO, $NO_2$, and $NH_3$ are converted into NO, and after conversion thereof, the NO is decomposed, and a generated amount or a concentration of 02 is measured. Therefore, although the total amount of NO, $NO_2$, and $NH_3$ can be measured, it is not possible to distinguish between these respective components.

Although the oxide semiconductor electrodes described in Japanese Laid-Open Patent Publication No. 2013-068632 and Japanese Laid-Open Patent Publication 2009-243942 are excellent in terms of the selectivity of NO and $NO_2$, on the other hand, since the sensitivity output characteristics with respect to NO and $NO_2$ are opposite in polarity, under an atmosphere in which both NO and $NO_2$ coexist, it has not been possible to correctly measure the concentration of NO or $NO_2$.

In the sensor described in Japanese Laid-Open Patent Publication No. 2009-511859 (PCT), it is difficult to accurately measure an $NH_3$ concentration over a prolonged time period, due to the instability of the oxide semiconductor electrode within the exhaust gas, and the weak adhesion strength with the substrate.

The present invention has been devised taking into consideration the aforementioned problems, and has the object of providing a gas sensor and a method of measuring concentrations of a plurality of target components in a gas to be measured, in which it is possible to accurately measure over a prolonged time period the concentration of a non-combusted component such as exhaust gas, and a plurality of components (for example, NO, $NO_2$, and $NH_3$) that coexist in the presence of oxygen.

[1] A gas sensor according to a first aspect of the present invention comprises a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, an oxygen concentration control unit adapted to control the oxygen concentration in the oxygen concentration adjustment chamber, a temperature control unit adapted to control a temperature of the sensor element, a condition setting unit adapted to set at least one of the oxygen concentration of the oxygen concentration adjustment chamber and the temperature of the sensor element to a condition that corresponds with a type of target component of the gas to be measured that was introduced, and a concentration calculation unit adapted to calculate concentrations of a plurality of respective different target components, on the basis of respective sensor outputs obtained under a plurality of conditions corresponding to types of the target components.

[2] In the first aspect of the present invention, the oxygen concentration adjustment chamber may include a main adjustment chamber communicating with the gas introduction port, and an auxiliary adjustment chamber communicating with the main adjustment chamber, and the measurement chamber may communicate with the auxiliary adjustment chamber.

[3] In the first aspect of the present invention, a pump electrode may be included inside the oxygen concentration adjustment chamber, a measurement electrode may be included inside the measurement chamber, and the pump electrode may be constituted by a material having a catalytic activity lower than that of the measurement electrode.

[4] In the first aspect of the present invention, the plurality of target components may be NO and $NO_2$.

[5] In this case, the respective concentrations of NO and $NO_2$ may be calculated in the following manner. More specifically, the condition setting unit sets as a first condition a condition for converting all of the $NO_2$ into NO, without causing decomposition of the NO. The condition setting unit sets as a second condition a condition for converting a portion of the $NO_2$ into NO, without causing decomposition of the NO. The concentration calculation unit calculates the respective concentrations of NO and $NO_2$ based on a first relational expression and a second relational expression. In this instance, the first relational expression expresses a relationship between NO, $NO_2$, and an offset current which constitutes a sensor output under the first condition. The second relational expression expresses a relationship between NO, $NO_2$, and an offset current which constitutes a sensor output under the second condition.

[6] Alternatively, the concentrations of NO and $NO_2$ may be calculated in the following manner. More specifically, the condition setting unit sets as a first condition a condition for converting all of the $NO_2$ into NO, without causing decomposition of the NO. The condition setting unit sets as a second condition a condition for converting a portion of the $NO_2$ into NO, without causing decomposition of the NO. The concentration calculation unit utilizes a first map. In the first map, from the sensor output under the first condition which is obtained experimentally in advance, and an output difference which is obtained by subtracting the sensor output under the first condition from the sensor output under the second condition, there is recorded a relationship between the NO concentration and the $NO_2$ concentration respectively for each of points specified by the sensor output under the first condition and the output difference. In addition, the concentration calculation unit determines the respective concentrations of NO and $NO_2$ by comparing with the first map the sensor output under the first condition during actual use, and the output difference obtained by subtracting the sensor output under the first condition from the sensor output under the second condition.

[7] In either of aspects [5] or [6], the condition setting unit preferably sets the second condition after having set the first condition.

[8] In the first aspect of the present invention, the plurality of target components may be NO, $NO_2$, and $NH_3$.

[9] In this case, the respective concentrations of NO, $NO_2$, and $NH_3$ may be calculated in the following manner. More specifically, the condition setting unit sets as a first condition a condition for converting all of the $NO_2$ into NO, and for converting all of the $NH_3$ into NO, without causing decomposition of the NO. The condition setting unit sets as a second condition a condition for converting a portion of the $NO_2$ into NO, and for converting all of the $NH_3$ into NO, without causing decomposition of the NO. The condition setting unit sets as a third condition a condition for converting $NO_2$ into NO, and for converting a portion of the $NH_3$ into NO, while causing decomposition of a portion of the NO. The concentration calculation unit calculates the respective concentrations of NO, $NO_2$, and $NH_3$ based on a third relational expression, a fourth relational expression, and a fifth rotational expression. In this instance, the third relational expression expresses a relationship between NO, $NO_2$, $NH_3$, and an offset current which constitutes a sensor output under the first condition. The fourth relational expression expresses a relationship between NO, $NO_2$, $NH_3$, and an offset current which constitutes a sensor output under the second condition. The fifth relational expression expresses a relationship between NO, $NO_2$, $NH_3$, and an offset current which constitutes a sensor output under the third condition.

[10] Alternatively, the respective concentrations of NO, $NO_2$, and $NH_3$ may be calculated in the following manner. More specifically, the condition setting unit sets as a first condition a condition for converting all of the $NO_2$ into NO, and for converting all of the $NH_3$ into NO, without causing decomposition of the NO. The condition setting unit sets as a second condition a condition for converting a portion of the $NO_2$ into NO, and for converting all of the $NH_3$ into NO, without causing decomposition of the NO. The condition setting unit sets as a third condition a condition for converting $NO_2$ into NO, and for converting a portion of the $NH_3$ into NO, while causing decomposition of a portion of the NO. The concentration calculation unit utilizes a second map. In the second map, from the sensor output under the first condition which is obtained experimentally in advance, a first output difference which is obtained by subtracting the sensor output under the first condition from the sensor output under the second condition, and a second output difference which is obtained by subtracting the sensor output under the second condition from the sensor output under the third condition, there is recorded a relationship between the NO concentration, the $NO_2$ concentration, and the $NH_3$ concentration respectively for each of points specified by the sensor output under the first condition, the first output difference, and the second output difference. In addition, the concentration calculation unit determines the respective concentrations of NO, $NO_2$, and $NH_3$ by comparing with the second map the sensor output under the first condition during actual use, the first output difference during actual use obtained by subtracting the sensor output under the first condition during actual use from the sensor output under the second condition during actual use, and the second output difference during actual use obtained by subtracting the sensor output under the second condition during actual use from the sensor output under the third condition during actual use.

[11] In either of aspects [9] or [10], the condition setting unit preferably sets the second condition after having set the first condition, and thereafter, preferably sets the third condition.

[12] In a method of measuring concentrations of a plurality of target components in a gas to be measured according to a second aspect of the present invention, there is used a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, the method comprising a condition setting step of setting at least one of the oxygen concentration of the oxygen concentration adjustment chamber and the temperature of the sensor element to a condition that corresponds with a type of target component of the gas to be measured that was introduced, and a concentration calculation step of calculating concentrations of a plurality of respective different target components, on the basis of respective sensor outputs obtained under a plurality of conditions corresponding to types of the target components.

[13] In the second aspect of the present invention, the plurality of target components may be NO and $NO_2$.

[14] In this case, the respective concentrations of NO and $NO_2$ may be calculated in the following manner. More specifically, in the condition setting step, there is set as a first condition a condition for converting all of the $NO_2$ into NO, without causing decomposition of the NO. In the condition setting step, there is set as a second condition a condition for converting a portion of the $NO_2$ into NO, without causing decomposition of the NO. In the concentration calculation step, the respective concentrations of NO and $NO_2$ are calculated based on a first relational expression and a second relational expression. In this instance, the first relational expression expresses a relationship between NO, $NO_2$, and an offset current which constitutes a sensor output under the first condition. The second relational expression expresses a relationship between NO, $NO_2$, and an offset current which constitutes a sensor output under the second condition.

[15] Alternatively, the concentrations of NO and $NO_2$ may be calculated in the following manner. More specifically, in the condition setting step, there is set as a first condition a condition for converting all of the $NO_2$ into NO, without causing decomposition of the NO. In the condition setting step, there is set as a second condition a condition for converting a portion of the $NO_2$ into NO, without causing decomposition of the NO. In the concentration calculation step, a first map is utilized. In the first map, from the sensor output under the first condition which is obtained experimentally in advance, and an output difference which is obtained by subtracting the sensor output under the first condition from the sensor output under the second condition, there is recorded a relationship between the NO concentration and the $NO_2$ concentration respectively for each of points specified by the sensor output under the first condition and the output difference. In addition, in the concentration calculation step, the respective concentrations of NO and $NO_2$ are determined by comparing with the first map the sensor output under the first condition during actual use, and the output difference obtained by subtracting the sensor output under the first condition from the sensor output under the second condition.

[16] In either of aspects [14] or [15], in the condition setting step, the second condition is preferably set after having set the first condition.

[17] In the second aspect of the present invention, the plurality of target components may be NO, $NO_2$, and $NH_3$.

[18] In this case, the respective concentrations of NO, $NO_2$, and $NH_3$ may be calculated in the following manner. More specifically, in the condition setting step, there is set as a first condition a condition for converting all of the $NO_2$ into NO, and for converting all of the $NH_3$ into NO, without causing decomposition of the NO. In the condition setting step, there is set as a second condition a condition for converting a portion of the $NO_2$ into NO, and for converting all of the $NH_3$ into NO, without causing decomposition of the NO. In the condition setting step, there is set as a third condition a condition for converting $NO_2$ into NO, and for converting a portion of the $NH_3$ into NO, while causing decomposition of a portion of the NO. In the concentration calculation step, the respective concentrations of NO, $NO_2$, and $NH_3$ are calculated based on a third relational expression, a fourth relational expression, and a fifth rotational expression. In this instance, the third relational expression expresses a relationship between NO, $NO_2$, $NH_3$, and an offset current which constitutes a sensor output under the first condition. The fourth relational expression expresses a relationship between NO, $NO_2$, $NH_3$, and an offset current which constitutes a sensor output under the second condition. The fifth relational expression expresses a relationship between NO, $NO_2$, $NH_3$, and an offset current which constitutes a sensor output under the third condition.

[19] Alternatively, the respective concentrations of NO, $NO_2$, and $NH_3$ may be calculated in the following manner. More specifically, in the condition setting step, there is set as a first condition a condition for converting all of the $NO_2$ into NO, and for converting all of the $NH_3$ into NO, without causing decomposition of the NO. In the condition setting step, there is set as a second condition a condition for converting a portion of the $NO_2$ into NO, and for converting all of the $NH_3$ into NO, without causing decomposition of the NO. In the condition setting step, there is set as a third condition a condition for converting $NO_2$ into NO, and for converting a portion of the $NH_3$ into NO, while causing decomposition of a portion of the NO. In the concentration calculation step, a second map is utilized. In the second map, from the sensor output under the first condition which is obtained experimentally in advance, a first output difference which is obtained by subtracting the sensor output under the first condition from the sensor output under the second condition, and a second output difference which is obtained by subtracting the sensor output under the second condition from the sensor output under the third condition, there is recorded a relationship between the NO concentration, the $NO_2$ concentration, and the $NH_3$ concentration respectively for each of points specified by the sensor output under the first condition, the first output difference, and the second output difference. In addition, in the concentration calculation step, the respective concentrations of NO, $NO_2$, and $NH_3$ are determined by comparing with the second map the sensor output under the first condition during actual use, the first output difference during actual use obtained by subtracting the sensor output under the first condition during actual use from the sensor output under the second condition during actual use, and the second output difference during actual use obtained by subtracting the sensor output under the second condition during actual use from the sensor output under the third condition during actual use.

[20] In either of aspects [18] or [19], in the condition setting step, the second condition is preferably set after having set the first condition, and thereafter, the third condition is preferably set.

In accordance with the gas sensor and the method of measuring concentrations of a plurality of target components in a gas to be measured according to the present invention, it is possible to accurately measure over a prolonged time period the concentration of a non-combusted component such as exhaust gas, and a plurality of components (for example, NO, $NO_2$, and $NH_3$) that coexist in the presence of oxygen.

BRIEF DESCRIPTION OF DRAWINGS

FIG. 3A shows a relationship between decomposition and non-decomposition of NO, whereas FIG. 3B shows a relationship between decomposition and non-decomposition of $NO_2$;

FIG. 9 is an explanatory diagram showing the first map utilized by the second gas sensor in the form of a table;

FIG. 11A shows a relationship between decomposition and non-decomposition of NO, whereas FIG. 11B shows a relationship between decomposition and non-decomposition of $NO_2$;

FIG. 20 is an explanatory diagram showing the second map utilized by the second gas sensor in the form of a table;

DESCRIPTION OF EMBODIMENTS

Embodiments of a gas sensor according to the present invention, and a method for measuring concentrations of a plurality of target components in a gas to be measured will be presented and described below with reference to FIGS. 1 to 23. In the present specification, the term "to" when used to indicate a numerical range is used with the implication of including the numerical values written before and after the term as a lower limit value and an upper limit value of the numerical range.

Figure 1:
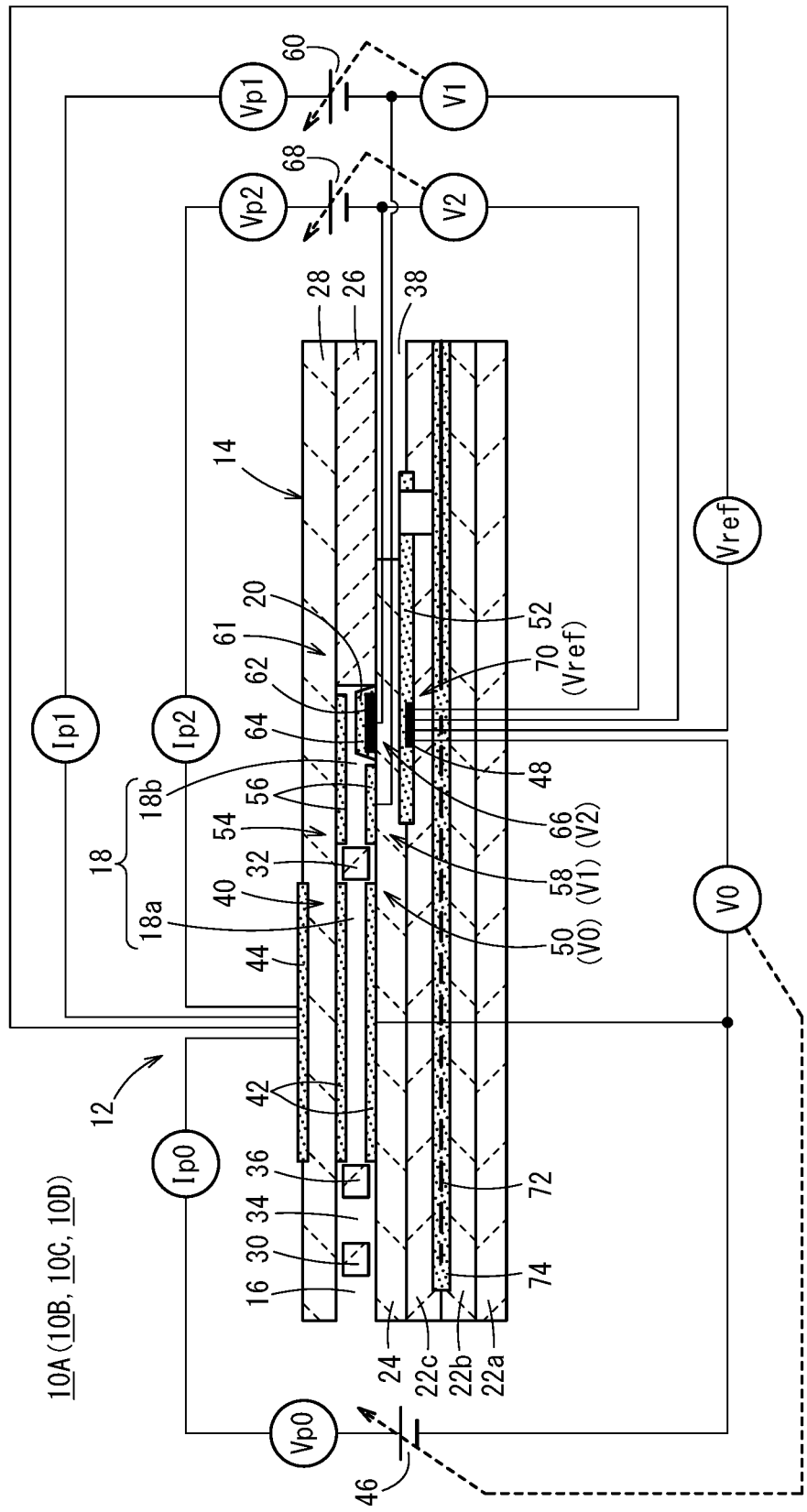
FIG. 1 is a cross-sectional view in which there is shown one structural example of a gas sensor (first gas sensor) according to a first embodiment through a gas sensor (fourth gas sensor) according to a fourth embodiment.
Figure 2:
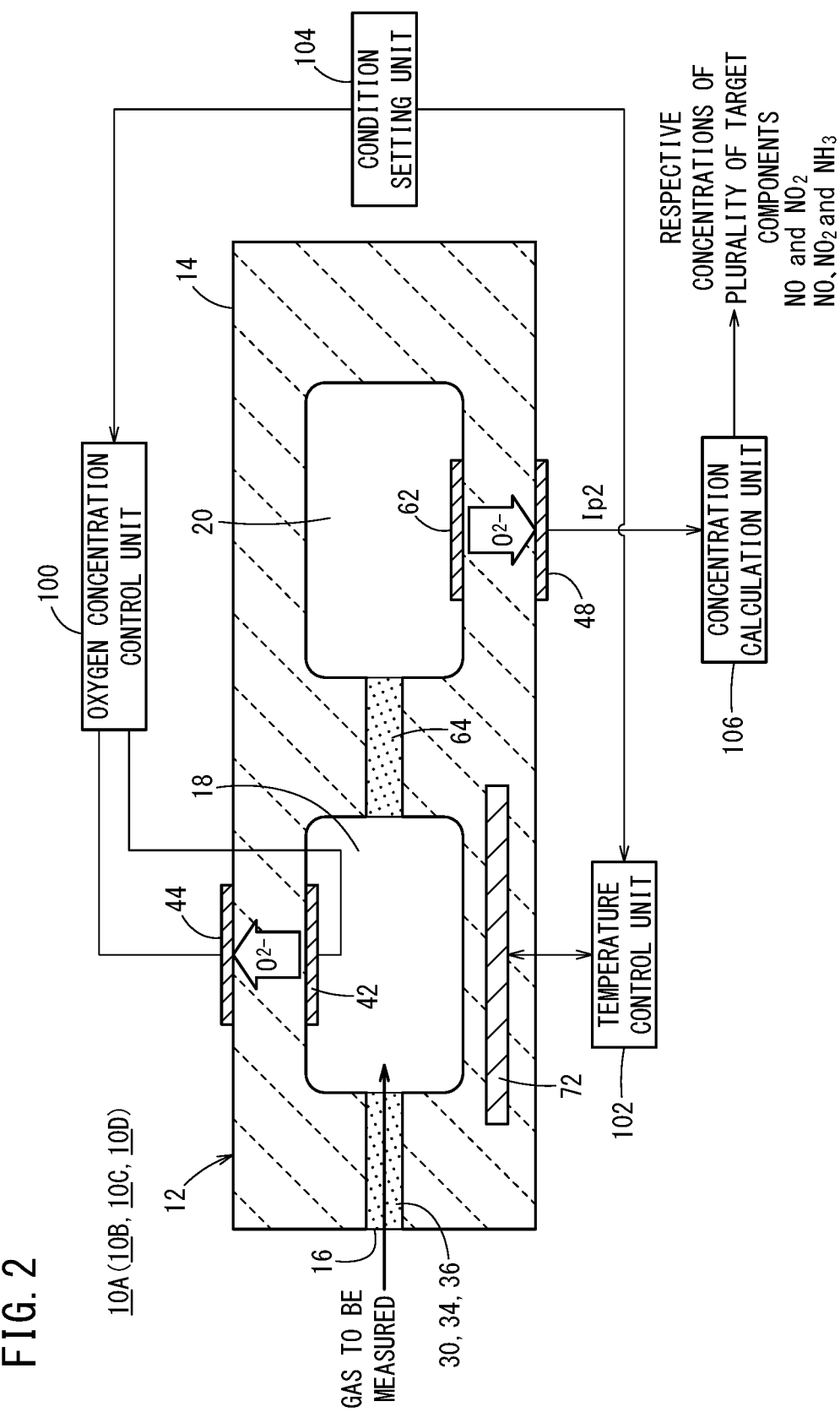
FIG. 2 is a configuration diagram schematically showing a first gas sensor through a fourth gas sensor.

First, as shown in FIGS. 1 and 2, a gas sensor (hereinafter referred to as a first gas sensor 10A) according to a first embodiment includes a sensor element 12. The sensor element 12 includes a structural body 14 made up from a solid electrolyte that exhibits at least oxygen ion conductivity, a gas introduction port 16 formed in the structural body 14 and into which a gas to be measured is introduced, an oxygen concentration adjustment chamber 18 formed in the structural body 14 and communicating with the gas introduction port 16, and a measurement chamber 20 formed in the structural body 14 and communicating with the oxygen concentration adjustment chamber 18.

The oxygen concentration adjustment chamber 18 includes a main adjustment chamber 18a communicating with the gas introduction port 16, and an auxiliary adjustment chamber 18b communicating with the main adjustment chamber 18a. The measurement chamber 20 communicates with the auxiliary adjustment chamber 18b.

More specifically, the structural body 14 of the sensor element 12 is constituted by six layers including a first substrate layer 22a, a second substrate layer 22b, a third substrate layer 22c, a first solid electrolyte layer 24, a spacer layer 26, and a second solid electrolyte layer 28, which are stacked in this order from a lower side as viewed in the drawing. The respective layers are composed respectively of an oxygen ion conductive solid electrolyte layer such as zirconia ($ZrO_2$) or the like.

Between a lower surface of the second solid electrolyte layer 28 and an upper surface of the first solid electrolyte layer 24 on a distal end side of the sensor element 12, there are provided the gas introduction port 16, a first diffusion rate control portion 30, the main adjustment chamber 18a, a second diffusion rate control portion 32, and an auxiliary adjustment chamber 18b. Furthermore, a buffer space 34 and a third diffusion rate control portion 36 may be provided between the first diffusion rate control portion 30 and the oxygen concentration adjustment chamber 18. The gas introduction port 16, the first diffusion rate control portion 30, the buffer space 34, the third diffusion rate control portion 36, the main adjustment chamber 18a, the second diffusion rate control portion 32, and the auxiliary adjustment chamber 18b are formed adjacent to each other in a manner communicating in this order. The portion from the gas introduction port 16 leading to the auxiliary adjustment chamber 18b is also referred to as a gas flow section.

The gas introduction port 16, the buffer space 34, the main adjustment chamber 18a, and the auxiliary adjustment chamber 18b are internal spaces which are disposed in a manner so that the spacer layer 26 is hollowed out. Any of the buffer space 34, the main adjustment chamber 18a, and the auxiliary adjustment chamber 18b is arranged in a manner so that respective upper parts thereof are defined by a lower surface of the second solid electrolyte layer 28, respective lower parts thereof are defined by an upper surface of the first solid electrolyte layer 24, and respective side parts thereof are defined by side surfaces of the spacer layer 26.

Any of the first diffusion rate control portion 30, the second diffusion rate control portion 32, and the third diffusion rate control portion 36 is provided as two horizontally elongated slits (in which the direction perpendicular to the drawing is the longitudinal direction of openings thereof).

Further, a reference gas introduction space 38 is disposed between an upper surface of the third substrate layer 22c and a lower surface of the spacer layer 26, at a position that is farther from the distal end side than the gas flow section. The reference gas introduction space 38 is an internal space in which an upper part thereof is defined by a lower surface of the spacer layer 26, a lower part thereof is defined by an upper surface of the third substrate layer 22c, and a side part thereof is defined by a side surface of the first solid electrolyte layer 24. For example, oxygen or atmospheric air is introduced as a reference gas into the reference gas introduction space 38.

The gas introduction port 16 is a location that opens with respect to the external space, and the target gas to be measured is drawn into the sensor element 12 from the external space through the gas introduction port 16.

The first diffusion rate control portion 30 is a location that imparts a predetermined diffusion resistance with respect to the gas to be measured which is drawn in from the gas introduction port 16.

The buffer space 34 is provided for the purpose of canceling fluctuations in the concentration of the gas to be measured, which are caused by pressure fluctuations of the gas to be measured in the external space (pulsations in the exhaust pressure, in the case that the gas to be measured is an exhaust gas of an automobile). Moreover, it should be noted that the sensor element 12 may or may not be equipped with the buffer space 34.

The third diffusion rate control portion 36 is a location that imparts a predetermined diffusion resistance to the gas to be measured which is drawn into the main adjustment chamber 18a from the buffer space 34. The third diffusion rate control portion 36 is provided in an accompanying manner with the provision of the buffer space 34.

In the case that the buffer space 34 and the third diffusion rate control portion 36 are not provided, the first diffusion rate control portion 30 and the main adjustment chamber 18a communicate directly with each other.

The main adjustment chamber 18a is provided as a space for the purpose of adjusting an oxygen partial pressure within the gas to be measured that is introduced from the gas introduction port 16. The oxygen partial pressure is adjusted by operation of a main pump cell 40.

The main pump cell 40 comprises an electrochemical pump cell (main electrochemical pumping cell), which is constituted by a main interior side pump electrode 42, an exterior side pump electrode 44, and an oxygen ion conductive solid electrolyte which is sandwiched between the two pump electrodes. The main interior side pump electrode 42 is provided substantially over the entire surface of an upper surface of the first solid electrolyte layer 24, a lower surface of the second solid electrolyte layer 28, and side surfaces of the spacer layer 26 that define the main adjustment chamber 18a. The exterior side pump electrode 44 is provided in a condition of being exposed to the external space in a region corresponding to the main interior side pump electrode 42 on the upper surface of the second solid electrolyte layer 28. The main interior side pump electrode 42 and the exterior side pump electrode 44 are made of a material that weakens the reduction capability with respect to the NOx component within the gas to be measured. For example, the pump electrodes are formed as porous cermet electrodes (for example, cermet electrodes of $ZrO_2$ and a noble metal such as Pt containing 0.1 to 30.0 wt % of Au) having rectangular shapes as viewed in plan.

The main pump cell 40 applies a pump voltage Vp0 supplied from a first variable power source 46 which is provided externally of the sensor element 12, and by allowing a pump current Ip0 to flow between the exterior side pump electrode 44 and the main interior side pump electrode 42, it is possible to pump oxygen in the interior of the main adjustment chamber 18a into the external space, or alternatively, to pump oxygen in the external space into the main adjustment chamber 18a.

Further, the sensor element 12 includes a first oxygen partial pressure detecting sensor cell 50 which is an electrochemical sensor cell. The first oxygen partial pressure detecting sensor cell 50 is constituted by the main interior side pump electrode 42, a reference electrode 48 sandwiched between the first solid electrolyte layer 24 and an upper surface of the third substrate layer 22c, and an oxygen ion conductive solid electrolyte sandwiched between these electrodes. The reference electrode 48 is an electrode having a substantially rectangular shape as viewed in plan, which is made from a porous cermet in the same manner as the exterior side pump electrode 44 and the like. Further, around the periphery of the reference electrode 48, a reference gas introduction layer 52 is provided, which is made from porous alumina and is connected to the reference gas introduction space 38. More specifically, the reference gas in the reference gas introduction space 38 is introduced to the surface of the reference electrode 48 via the reference gas introduction layer 52. The first oxygen partial pressure detecting sensor cell 50 generates an electromotive force V0 between the main interior side pump electrode 42 and the reference electrode 48, which is caused by the difference in oxygen concentration between the atmosphere in the interior of the main adjustment chamber 18a and the reference gas in the reference gas introduction space 38.

The electromotive force V0 generated in the first oxygen partial pressure detecting sensor cell 50 changes depending on the oxygen partial pressure of the atmosphere existing in the main adjustment chamber 18a. In accordance with the electromotive force V0, the sensor element 12 feedback-controls the first variable power source 46 of the main pump cell 40. Consequently, the pump voltage Vp0, which is applied by the first variable power source 46 to the main pump cell 40, can be controlled in accordance with the oxygen partial pressure of the atmosphere in the main adjustment chamber 18a.

The second diffusion rate control portion 32 imparts a predetermined diffusion resistance to the gas to be measured, the oxygen concentration (oxygen partial pressure) of which is controlled by operation of the main pump cell 40 in the main adjustment chamber 18a, and is located at a site leading to the auxiliary adjustment chamber 18b.

The auxiliary adjustment chamber 18b is provided as a space for further carrying out adjustment of the oxygen partial pressure by an auxiliary pump cell 54, with respect to the gas to be measured which is introduced through the second diffusion rate control portion 32, after the oxygen concentration (oxygen partial pressure) has been adjusted beforehand in the main adjustment chamber 18a. In accordance with this feature, the oxygen concentration inside the auxiliary adjustment chamber 18b can be kept constant with high accuracy, and therefore, the first gas sensor 10A is made capable of measuring the NOx concentration with high accuracy.

The auxiliary pump cell 54 is an electrochemical pump cell, and is constituted by an auxiliary pump electrode 56, which is provided substantially over the entirety of the lower surface of the second solid electrolyte layer 28 facing toward the auxiliary adjustment chamber 18b, the exterior side pump electrode 44, and the second solid electrolyte layer 28.

Moreover, in the same manner as the main interior side pump electrode 42, the auxiliary pump electrode 56 is also formed using a material that weakens the reduction capability with respect to the NOx component within the gas to be measured.

The auxiliary pump cell 54, by applying a desired voltage Vp1 between the auxiliary pump electrode 56 and the exterior side pump electrode 44, is capable of pumping out oxygen within the atmosphere inside the auxiliary adjustment chamber 18b into the external space, or alternatively, is capable of pumping in oxygen from the external space into the auxiliary adjustment chamber 18b.

Further, in order to control the oxygen partial pressure within the atmosphere inside the auxiliary adjustment chamber 18b, an electrochemical sensor cell, and more specifically, a second oxygen partial pressure detecting sensor cell 58 for controlling the auxiliary pump, is constituted by the auxiliary pump electrode 56, the reference electrode 48, the second solid electrolyte layer 28, the spacer layer 26, and the first solid electrolyte layer 24.

Moreover, the auxiliary pump cell 54 carries out pumping by a second variable power source 60, the voltage of which is controlled based on an electromotive force V1 detected by the second oxygen partial pressure detecting sensor cell 58. Consequently, the oxygen partial pressure within the atmosphere in the auxiliary adjustment chamber 18b is controlled so as to become a low partial pressure that does not substantially influence the measurement of NOx.

Further, together therewith, a pump current $IP_1$ of the auxiliary pump cell 54 is used so as to control the electromotive force V0 of the first oxygen partial pressure detecting sensor cell 50. More specifically, the pump current $IP_1$ is input as a control signal to the first oxygen partial pressure detecting sensor cell 50, and by controlling the electromotive force V0 thereof, the gradient of the oxygen partial pressure within the gas to be measured, which is introduced from the second diffusion rate control portion 32 into the auxiliary adjustment chamber 18b, is controlled to remain constant at all times. When the first gas sensor 10A is used as an NOx sensor, by the actions of the main pump cell 40 and the auxiliary pump cell 54, the oxygen concentration inside the auxiliary adjustment chamber 18b is maintained at a predetermined value with high accuracy for each of the respective conditions.

Measurement of the NOx concentration is primarily performed by operations of a measurement pump cell 61. The measurement pump cell 61 is an electrochemical pump cell constituted by a measurement electrode 62, the exterior side pump electrode 44, the second solid electrolyte layer 28, the spacer layer 26, and the first solid electrolyte layer 24. The measurement electrode 62 is provided directly on an upper surface of the first solid electrolyte layer 24 in facing relation to the auxiliary adjustment chamber 18b, and is covered by a fourth diffusion rate control portion 64. The fourth diffusion rate control portion 64 is a film composed of a ceramic porous body such as alumina ($Al_2O_3$). The fourth diffusion rate control portion 64 fulfills a role of limiting the amount of NOx that flows into the measurement electrode 62. Further, the fourth diffusion rate control portion 64 also functions as a protective film for the measurement electrode 62. Accordingly, the surrounding periphery of the measurement electrode 62 functions as the measurement chamber 20. The measurement electrode 62 is a porous cermet electrode made of a material whose reduction capability with respect to the NOx component within the gas to be measured is higher than that of the main interior side pump electrode 42. The measurement electrode 62 also functions as an NOx reduction catalyst for reducing NOx existing within the atmosphere above the measurement electrode 62.

The measurement pump cell 61 is capable of pumping out oxygen that is generated by the decomposition of nitrogen oxide within the atmosphere around the periphery of the measurement electrode 62 (measurement chamber 20), and can detect the generated amount as the pump current $IP_2$, or stated otherwise, as the sensor output.

Further, in order to detect the oxygen partial pressure around the measurement electrode 62 (measurement chamber 20), an electrochemical sensor cell, and more specifically, a third oxygen partial pressure detecting sensor cell 66 for controlling the measurement pump, is constituted by the first solid electrolyte layer 24, the measurement electrode 62, and the reference electrode 48. A third variable power source 68 is controlled based on an electromotive force V2 detected by the third oxygen partial pressure detecting sensor cell 66.

The gas to be measured, which is introduced into the auxiliary adjustment chamber 18b, reaches the measurement electrode 62 through the fourth diffusion rate control portion 64, under a condition in which the oxygen partial pressure is controlled. Nitrogen oxide existing within the gas to be measured around the periphery of the measurement electrode 62 is reduced to thereby generate oxygen. Then, the generated oxygen is subjected to pumping by the measurement pump cell 61. At this time, the voltage Vp2 of the third variable power source 68 is controlled in a manner so that the electromotive force V2 detected by the third oxygen partial pressure detecting sensor cell 66 becomes constant. The amount of oxygen generated around the periphery of the measurement electrode 62 is proportional to the concentration of nitrogen oxide within the gas to be measured. Accordingly, the nitrogen oxide concentration within the gas to be measured can be calculated using the pump current $IP_2$ of the measurement pump cell 61.

Further, the first gas sensor 10A includes an electrochemical sensor cell 70. The sensor cell 70 includes the second solid electrolyte layer 28, the spacer layer 26, the first solid electrolyte layer 24, the third substrate layer 22c, the exterior side pump electrode 44, and the reference electrode 48. In accordance with the electromotive force Vref obtained by the sensor cell 70, it is possible to detect the oxygen partial pressure within the gas to be measured existing externally of the sensor.

Furthermore, in the sensor element 12, a heater 72 is formed in a manner of being sandwiched from above and below between the second substrate layer 22b and the third substrate layer 22c. The heater 72 generates heat by being supplied with power from the exterior through a non-illustrated heater electrode provided on a lower surface of the first substrate layer 22a. As a result of the heat generated by the heater 72, the oxygen ion conductivity of the solid electrolyte that constitutes the sensor element 12 is enhanced. The heater 72 is embedded over the entire region of the oxygen concentration adjustment chamber 18, and a predetermined location of the sensor element 12 can be heated and maintained at a predetermined temperature. Moreover, a heater insulating layer 74 made of alumina or the like is formed on the upper and lower surfaces of the heater 72, for the purpose of obtaining electrical insulation thereof from the second substrate layer 22b and the third substrate layer 22c.

Furthermore, as schematically shown in FIG. 2, the first gas sensor 10A includes an oxygen concentration control unit 100, a temperature control unit 102, a condition setting unit 104, and a concentration calculation unit 106. The oxygen concentration control unit 100 controls the oxygen concentration in the oxygen concentration adjustment chamber 18. The temperature control unit 102 controls the temperature of the sensor element 12. The condition setting unit 104 sets at least one of the oxygen concentration in the oxygen concentration adjustment chamber 18 and the temperature of the sensor element 12, to a condition corresponding to the type of target component of the gas to be measured that was introduced. The concentration calculation unit 106 calculates the concentrations of the plurality of different target components, on the basis of the respective sensor outputs obtained under a plurality of conditions corresponding to the types of target components.

Moreover, the oxygen concentration control unit 100, the temperature control unit 102, the condition setting unit 104, and the concentration calculation unit 106 are constituted by one or more electronic circuits having, for example, one or a plurality of CPUs (central processing units), memory devices, and the like. The electronic circuits are software-based functional units in which predetermined functions are realized, for example, by the CPUs executing programs stored in a storage device. Of course, the electronic circuits may be constituted by an integrated circuit such as an FPGA (Field-Programmable Gate Array), in which the plurality of electronic circuits are connected according to the functions thereof.

In the conventional technique, after having carried out conversion into NO with respect to all of the target components of NO and $NO_2$ existing inside the oxygen concentration adjustment chamber 18, the target components are introduced into the measurement chamber 20, and a total amount of the two components is measured. Stated otherwise, it has been impossible to measure the concentrations of the two target components, that is, the respective concentrations of NO and $NO_2$.

In contrast thereto, as described above, by being equipped with the oxygen concentration control unit 100, the temperature control unit 102, the condition setting unit 104, and the concentration calculation unit 106, the first gas sensor 10A is made capable of measuring the respective concentrations of NO and $NO_2$.

On the basis of the conditions set by the condition setting unit 104, and the electromotive force V0 generated in the first oxygen partial pressure detecting sensor cell 50 (see FIG. 1), the oxygen concentration control unit 100 feedback-controls the first variable power source 46, thereby adjusting the oxygen concentration inside the oxygen concentration adjustment chamber 18 to a concentration in accordance with the above-described conditions.

The temperature control unit 102 feedback-controls the heater 72 on the basis of the conditions set by the condition setting unit 104, and the measured value from a temperature sensor (not shown) that measures the temperature of the sensor element 12, whereby the temperature of the sensor element 12 is adjusted to a temperature in accordance with the above-described conditions.

The condition setting unit 104 sets as a first condition a condition for converting all of the $NO_2$ into NO, without causing decomposition of the NO, and further sets as a second condition a condition for converting a portion of the $NO_2$ into NO, without causing decomposition of the NO.

Figure 3A:
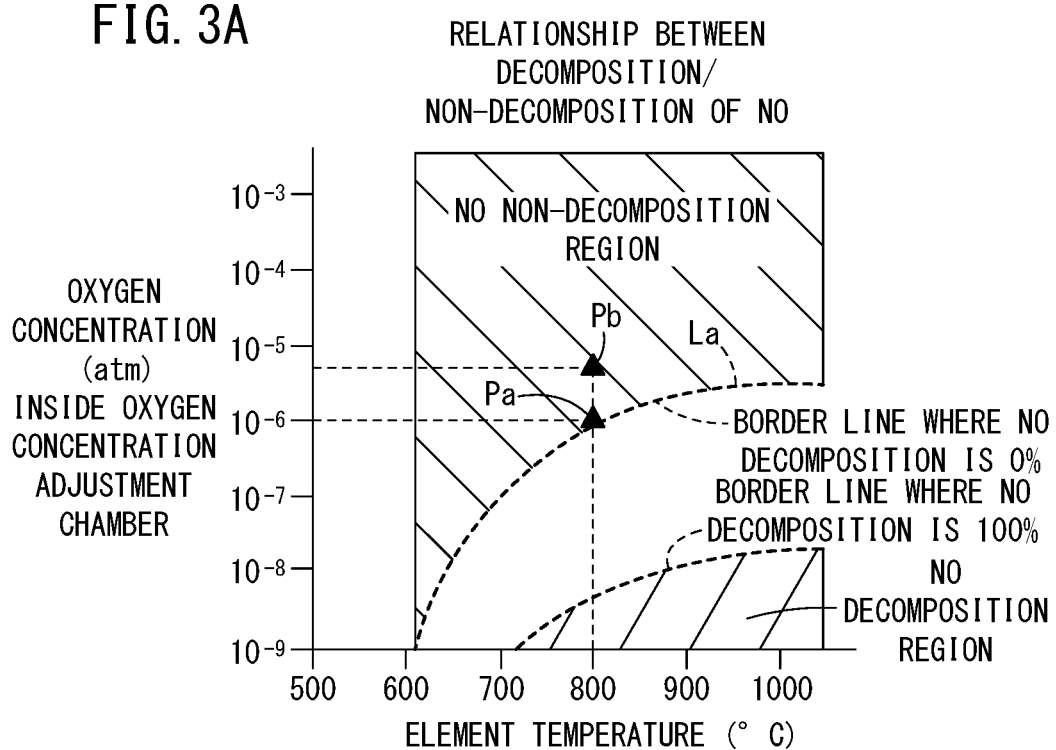
FIGS. 3A and 3B are diagrams showing oxygen concentration characteristics in an oxygen concentration adjustment chamber with respect to the temperature (element temperature) of a sensor element, and in particular.
Figure 3B:
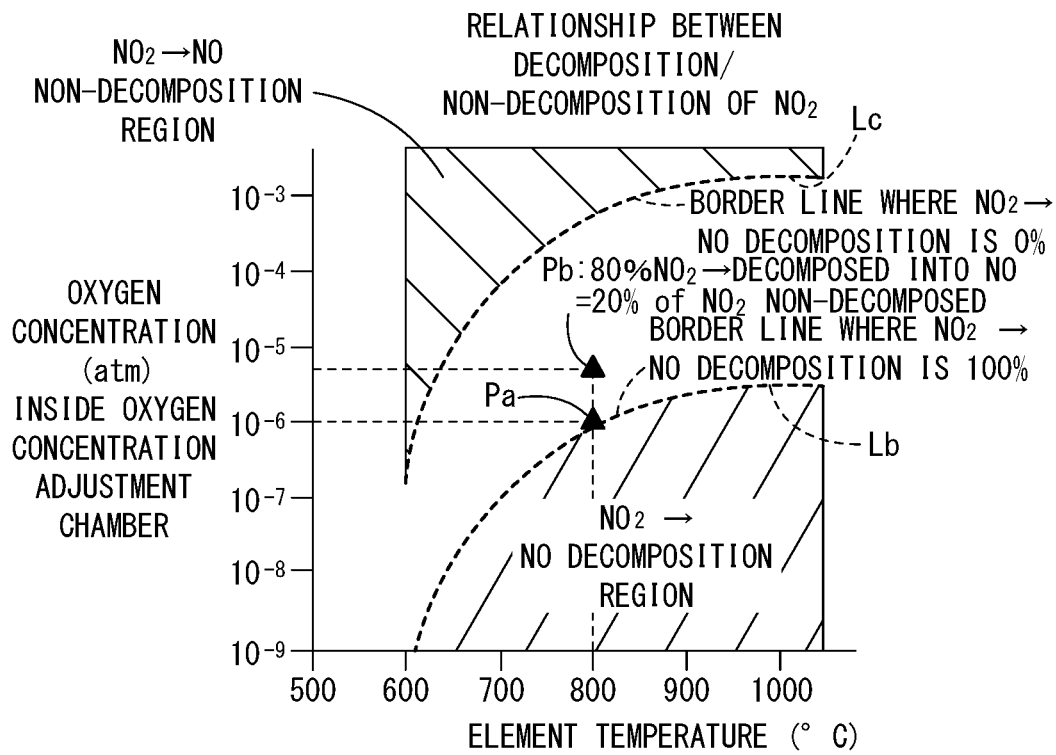

The first condition and the second condition will be described with reference to FIGS. 3A and 3B. FIGS. 3A and 3B are diagrams showing oxygen concentration characteristics inside the oxygen concentration adjustment chamber 18 with respect to the temperature of the sensor element 12, and in particular, FIG. 3A shows a relationship between decomposition and non-decomposition of NO, whereas FIG. 3B shows a relationship between decomposition and non-decomposition of $NO_2$.

In addition, in FIG. 3A, the first condition is set to a point Pa on a boundary line La where the NO decomposition rate is 0%. More specifically, as shown in FIG. 3B, the first condition is set to a point Pa on the boundary line Lb where the decomposition rate from $NO_2$ into NO is 100%. In FIG. 3A, the second condition is set to a point Pb within a region where the NO remains non-decomposed. More specifically, as shown in FIG. 3B, the point Pb is set between a boundary line Lb where the decomposition rate from $NO_2$ into NO is 100%, and a boundary line Lc where the decomposition rate from $NO_2$ into NO is 0%. For example, the second condition is set to a point Pb where 80% of the $NO_2$ is decomposed into NO, and 20% of the $NO_2$ remains non-decomposed. A change from the first condition to the second condition in the present embodiment is performed, for example, by changing the oxygen concentration inside the oxygen concentration adjustment chamber 18 while the temperature is kept constant. The setting of the measurement conditions as described above is merely an example, and the measurement conditions can be arbitrarily set insofar as they do not deviate from a concept in which "by replacing the setting conditions for the oxygen concentration and the temperature of the oxygen concentration adjustment chamber from the reference conditions, a change is made to the chemical equilibrium of the target components (NO, $NO_2$, $NH_3$) occurring in the oxygen concentration adjustment chamber, the sensor outputs obtained in the measurement chamber are intentionally changed, and the respective component concentrations are obtained from the sensor outputs under the reference conditions and the changed amount of the sensor outputs due to replacement of the conditions," which is the basic concept of the present invention. For example, the oxygen concentration in the oxygen concentration adjustment chamber 18 is kept constant while the temperature is changed, and the like.

It should be noted that, in FIG. 3A, the boundary line where the NO decomposition rate is 0% and the boundary line where the NO decomposition rate is 100% are not indicative of the absolute progress of the decomposition reaction. For example, considering the boundary line where the NO decomposition rate is 0%, a combination of the oxygen concentration of the oxygen concentration adjustment chamber 18 and the temperature of the measurement element is shown in which, even if the oxygen concentration in the oxygen concentration adjustment chamber 18 increases more than such a value, the slope (i.e., sensitivity coefficient) of the pump current $IP_2$ flowing to the measurement pump cell 61 that is arranged in the measurement chamber 20 with respect to the NO concentration does not increase. Further, considering the boundary line where the NO decomposition rate is 100%, a combination of the oxygen concentration of the oxygen concentration adjustment chamber 18 and the temperature of the measurement element is shown in which, even if the concentration of NO in the gas to be measured is increased, the pump current $IP_2$ flowing to the measurement pump cell 61 that is arranged in the measurement chamber 20 does not increase.

In order to change the boundary lines depending on the catalytic activity of the main interior side pump electrode 42 that is disposed inside the oxygen concentration adjustment chamber 18, and the microstructure of the electrode, experimental confirmations should be made for each of the element temperature, the electrode material, and the electrode microstructure.

In a similar manner, the boundary line where the $NO_2 \rightarrow NO$ decomposition rate is 0%, and the boundary line where the $NO_2 \rightarrow NO$ decomposition rate is 100% in FIG. 3B are not indicative of the absolute progress of the decomposition reaction. For example, considering the boundary line where the $NO_2 \rightarrow NO$ decomposition rate is 0%, a combination of the oxygen concentration of the oxygen concentration adjustment chamber 18 and the temperature of the measurement element is shown in which, even if the oxygen concentration in the oxygen concentration adjustment chamber 18 increases more than such a value, the slope (i.e., sensitivity coefficient) of the pump current $IP_2$ flowing to the measurement pump cell 61 that is arranged in the measurement chamber 20 with respect to the $NO_2$ concentration does not increase. Further, considering the boundary line where the $NO_2 \rightarrow NO$ decomposition rate is 100%, a combination of the oxygen concentration of the oxygen concentration adjustment chamber 18 and the temperature of the measurement element is shown in which, even if the oxygen concentration in the oxygen concentration adjustment chamber 18 decreases more than such a value, the slope (i.e., sensitivity coefficient) of the pump current $IP_2$ flowing to the measurement pump cell 61 that is arranged in the measurement chamber 20 with respect to the $NO_2$ concentration does not decrease.

The reaction inside the oxygen concentration adjustment chamber 18 and the reaction inside the measurement chamber 20 will be briefly described with reference to the schematic views shown in FIGS. 4 and 5 and the graphs shown in FIGS. 6A and 6B.

Figure 4:
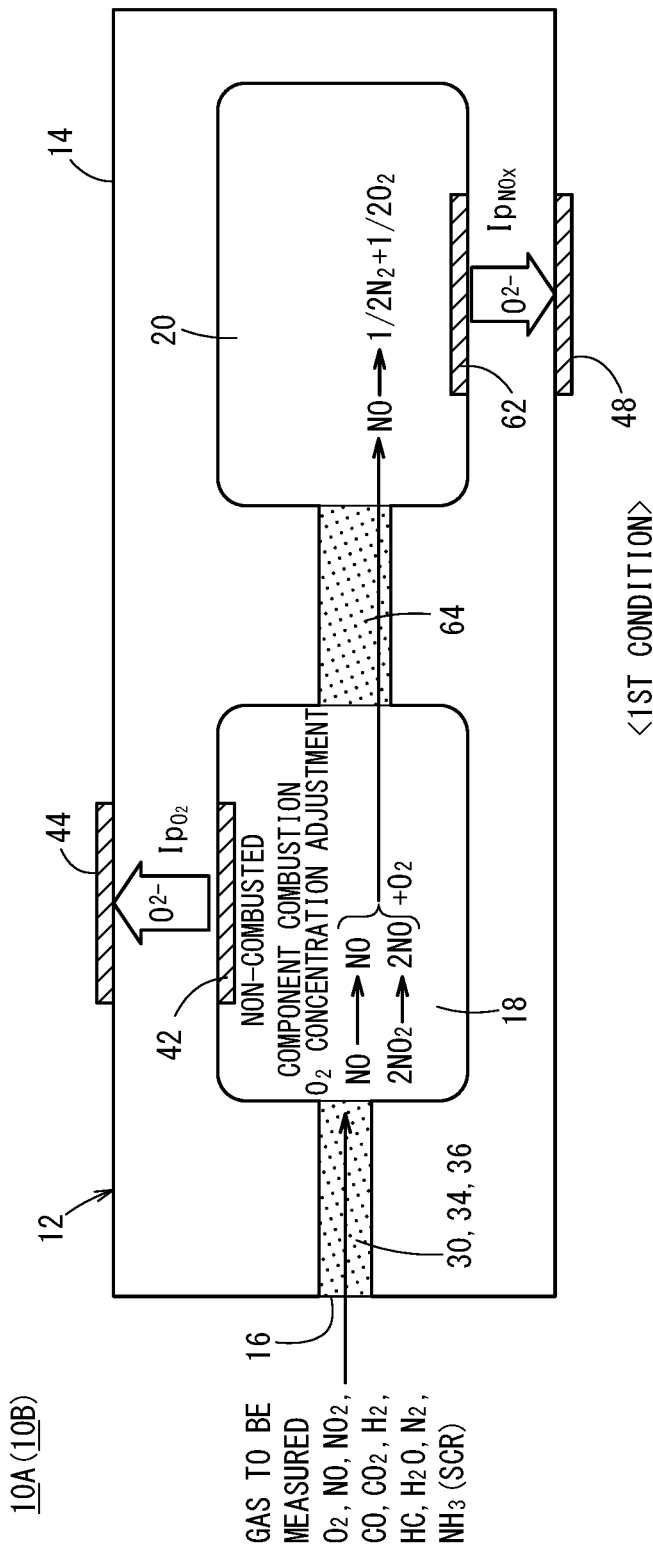
FIG. 4 is an explanatory diagram schematically showing a reaction in an oxygen concentration adjustment chamber and a reaction in a measurement chamber under a first condition, in a first gas sensor and a second gas sensor.

First, in the case of being set to the first condition, as shown in FIG. 4, NO is not decomposed inside the oxygen concentration adjustment chamber 18, but remains as is in the form of NO. On the other hand, in regards to $NO_2$, a decomposition reaction of $2NO_2 \rightarrow 2NO + O_2$ occurs. Accordingly, NO enters into the measurement chamber 20 from the oxygen concentration adjustment chamber 18, and $NO_2$ does not enter therein. Inside the measurement chamber 20, a decomposition reaction of $NO \rightarrow (\frac{1}{2})N_2 + (\frac{1}{2})O_2$ occurs, and among the products of the reaction, in accordance with the $O_2$ being pumped out, it is detected as a sensor output (pump current $IP_2$).

Figure 5:
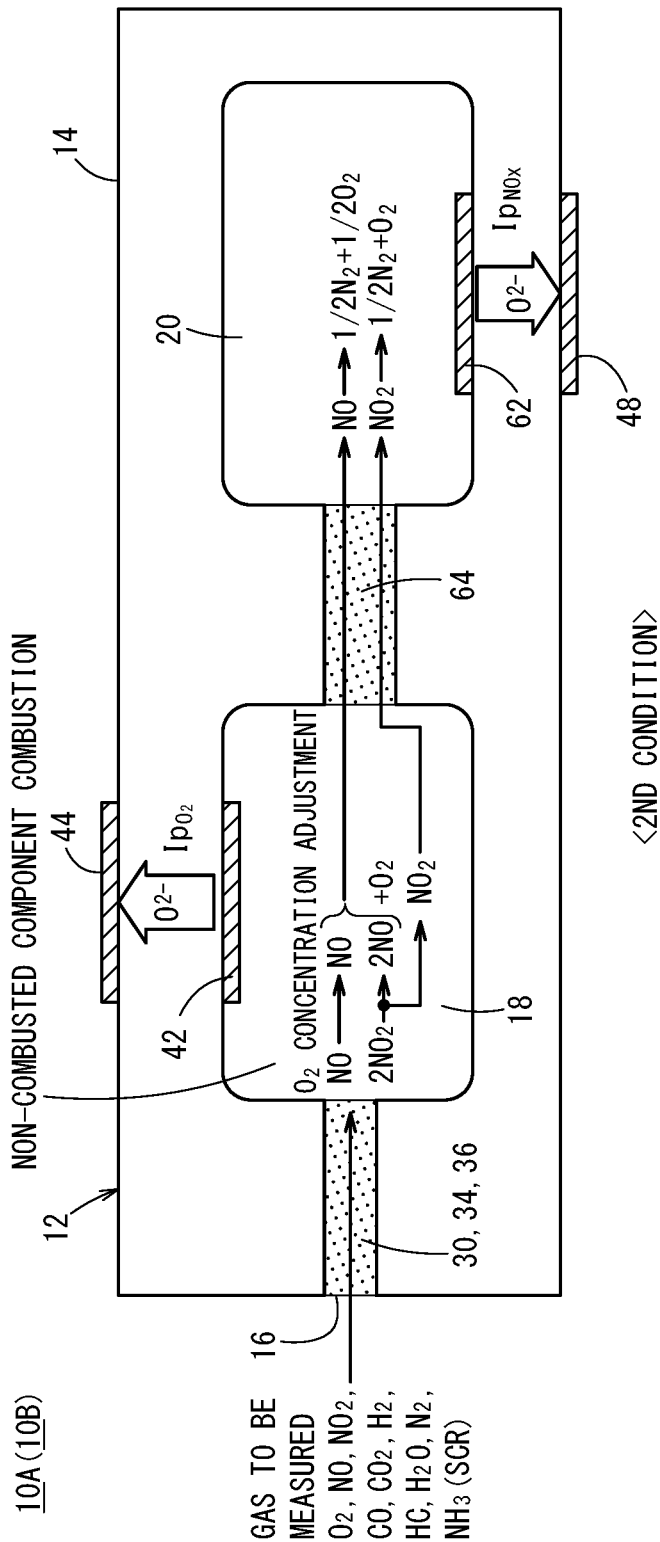
FIG. 5 is an explanatory diagram schematically showing a reaction in an oxygen concentration adjustment chamber and a reaction in a measurement chamber under a second condition, in the first gas sensor and the second gas sensor.

In the case of being set to the second condition, as shown in FIG. 5, NO is not decomposed inside the oxygen concentration adjustment chamber 18, but remains as is in the form of NO. On the other hand, concerning the $NO_2$, for example, 80% of the $NO_2$ is decomposed into NO by a decomposition reaction of $2NO_2 \rightarrow 2NO + O_2$, and the remaining 20% of the $NO_2$ is not decomposed. Accordingly, NO and $NO_2$ enter into the measurement chamber 20 from the oxygen concentration adjustment chamber 18. Inside the measurement chamber 20, a decomposition reaction of $NO \rightarrow (\frac{1}{2})N_2 + (\frac{1}{2})O_2$, and a decomposition reaction of $NO_2$ $(\frac{1}{2})N_2 + O_2$ occur. Among the products of the reactions, in accordance with the $O_2$ being pumped out, it is detected as a sensor output (pump current $IP_2$).

Figure 6A:
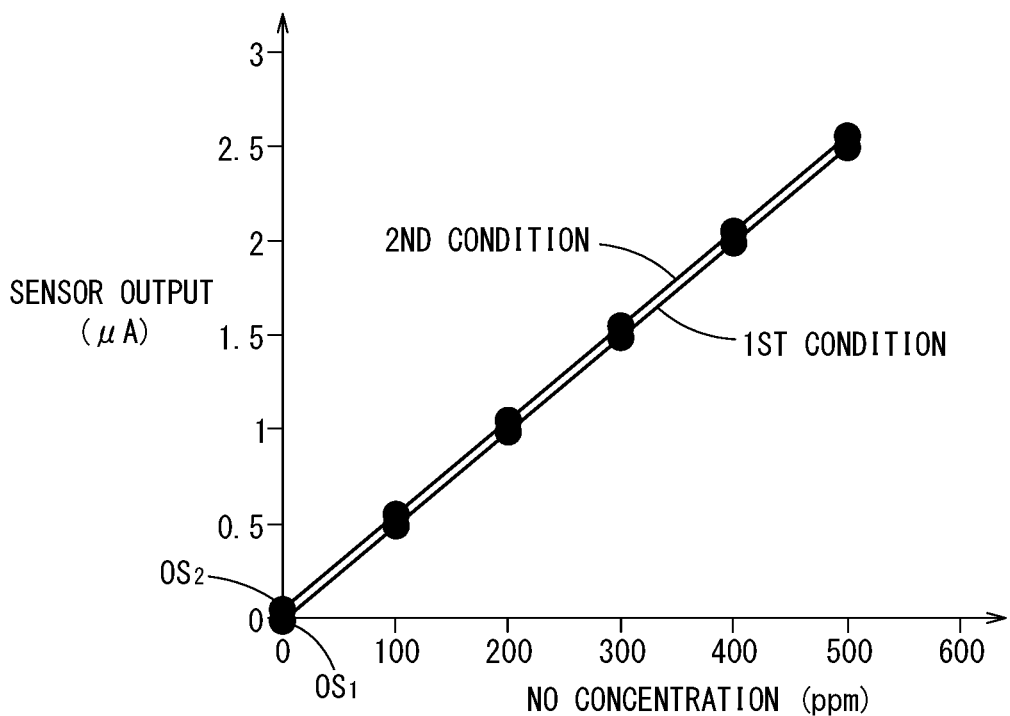
FIG. 6A is a graph showing sensor output characteristics with respect to NO concentration under the first condition, and sensor output characteristics with respect to NO concentration under the second condition.

In the case of only NO being introduced under the first condition, as shown in FIG. 6A, when the NO concentration is 0 ppm, in the sensor output with respect to the NO concentration, an offset current $OS_1$ appears corresponding to the oxygen concentration at the point Pa in FIGS. 3A and 3B. In addition, as the NO concentration rises, the sensor output also rises proportionally.

Figure 6B:
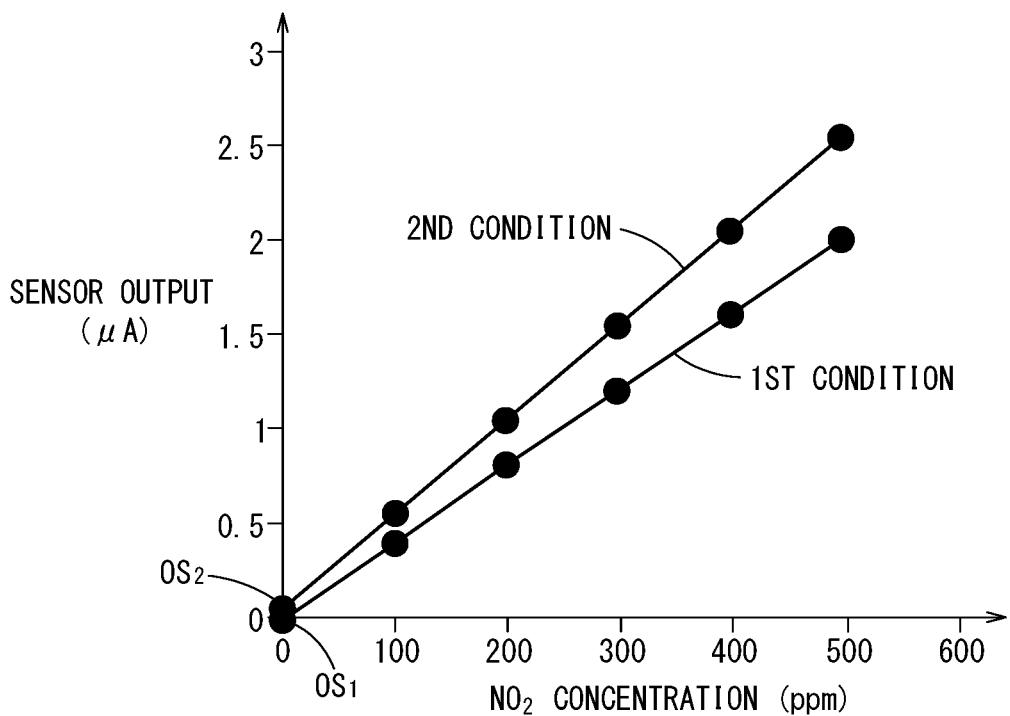
FIG. 6B is a graph showing sensor output characteristics with respect to $NO_2$ concentration under the first condition, and sensor output characteristics with respect to $NO_2$ concentration under the second condition.

In the case of only $NO_2$ being introduced under the first condition, as shown in FIG. 6B, when the $NO_2$ concentration is 0 ppm, in the sensor output with respect to the $NO_2$ concentration, an offset current $OS_1$ appears similar to the situation shown in FIG. 6A. Additionally, as the $NO_2$ concentration rises, the sensor output also rises proportionally, however, the slope thereof is smaller than the slope of the NO concentration under the first condition, due to the difference between the diffusion coefficients of NO and $NO_2$. When the slope of the NO concentration under the first condition is 1, the slope thereof is about 0.9.

Accordingly, a first relational expression (1) between the sensor output $IP_1$ under the first condition, and the sensor output (NO) corresponding to the NO concentration and the sensor output ($NO_2$) corresponding to the $NO_2$ concentration under the first condition is expressed in the following manner.

$$IP_1 = NO + 0.9NO_2 + OS_1 \qquad (1)$$

Similarly, in the case of only NO being introduced under the second condition, as shown in FIG. 6A, when the NO concentration is 0 ppm, in the sensor output with respect to the NO concentration, an offset current $OS_2$ appears corresponding to the oxygen concentration at the point Pb in FIG. 3B. In addition, as the NO concentration rises, the sensor output also rises proportionally. From the fact that only NO is introduced, the slope of the NO concentration is the same as in the case of the first condition.

In the case of only $NO_2$ being introduced under the second condition, as shown in FIG. 6B, when the $NO_2$ concentration is 0 ppm, in the sensor output with respect to the $NO_2$ concentration, an offset current $OS_2$ appears similar to the situation shown in FIG. 6A. Additionally, as the $NO_2$ concentration rises, the sensor output also rises proportionally, however, the slope thereof is greater than the slope of the NO concentration under the first condition. This is because the $NO_2$, which has arrived at the measurement chamber 20 without being decomposed, is then decomposed, whereby the amount of $O_2$ becomes greater than the amount at which NO is decomposed. When the slope of the NO concentration under the second condition is 1, the slope thereof is about 1.12.

Accordingly, a second relational expression (2) between the sensor output $IP_2$ under the second condition, and the sensor output (NO) corresponding to the NO concentration and the sensor output ($NO_2$) corresponding to the $NO_2$ concentration under the second condition is expressed in the following manner.

$$IP_2 = NO + 1.12NO_2 + OS_2 \qquad (2)$$

From the fact that both the offset currents $OS_1$ and $OS_2$ are constants, by simultaneously solving the binomial equations of the first relational expression (1) and the second relational expression (2), it is possible to calculate the NO concentration and the $NO_2$ concentration in the gas to be measured in which NO and $NO_2$ are mixed.

Next, the process of measuring NO and $NO_2$ by the first gas sensor 10A will be described with reference to the flowchart of FIG. 7.

Figure 7:
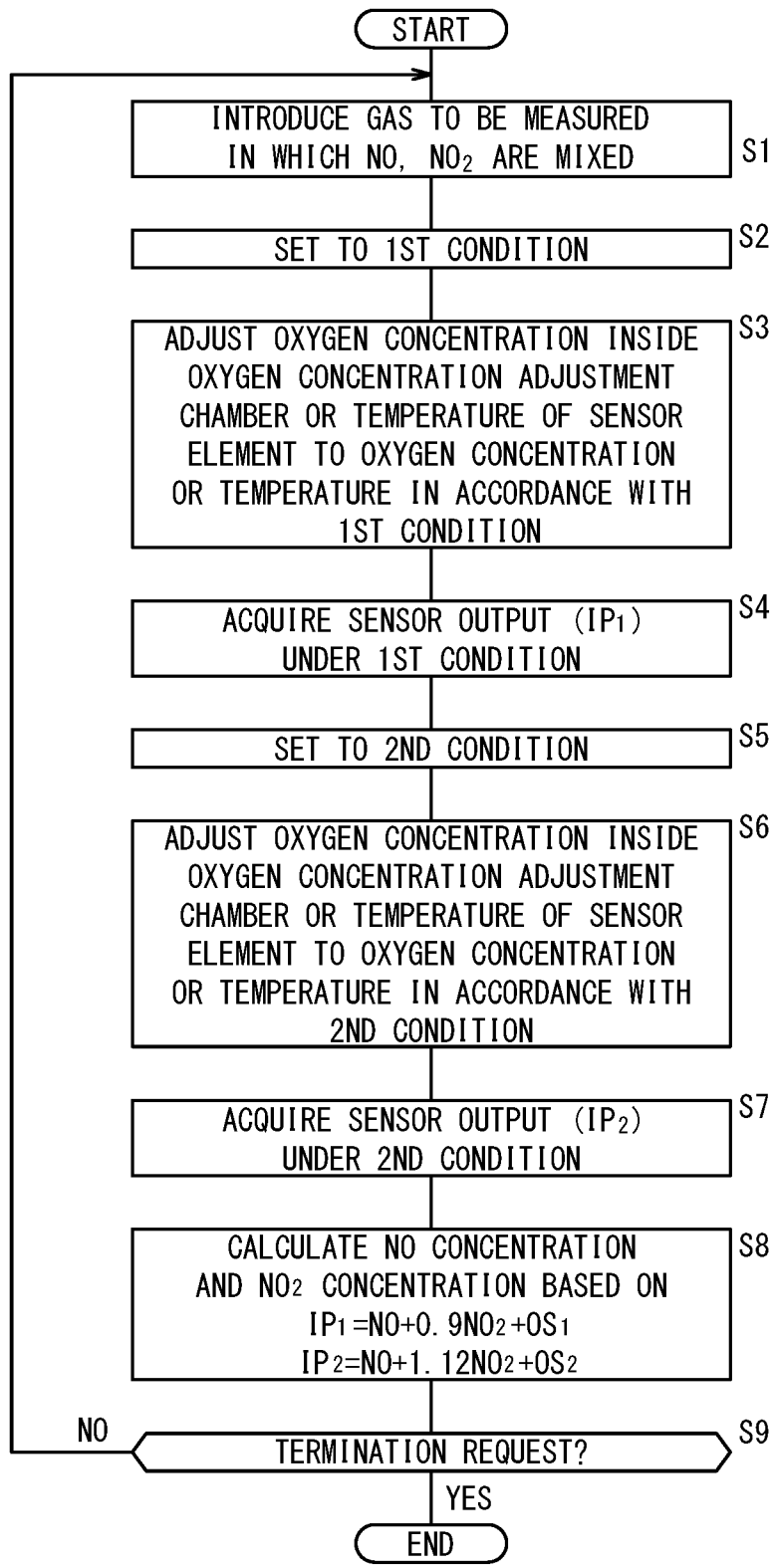
FIG. 7 is a flowchart showing a process of measuring NO and $NO_2$ by the first gas sensor.

First, in step S1 of FIG. 7, the first gas sensor 10A introduces a gas to be measured in which NO and $NO_2$ are mixed into the oxygen concentration adjustment chamber 18 through the gas introduction port 16.

In step S2, the condition setting unit 104 sets the first condition, and activates the oxygen concentration control unit 100 or the temperature control unit 102.

In step S3, the oxygen concentration control unit 100 or the temperature control unit 102 adjusts the oxygen concentration inside the oxygen concentration adjustment chamber 18 or the temperature of the sensor element 12 to an oxygen concentration or a temperature in accordance with the first condition.

In step S4, the concentration calculation unit 106 acquires the sensor output ($IP_1$) under the first condition.

In step S5, the condition setting unit 104 sets the second condition, and activates the oxygen concentration control unit 100 or the temperature control unit 102.

In step S6, the oxygen concentration control unit 100 or the temperature control unit 102 adjusts the oxygen concentration inside the oxygen concentration adjustment chamber 18 or the temperature of the sensor element 12 to an oxygen concentration or a sensor temperature in accordance with the second condition.

In step S7, the concentration calculation unit 106 acquires the sensor output ($IP_2$) under the second condition.

In step S8, by simultaneously solving the binomial equations of the first relational expression (1) and the second relational expression (2), the concentration calculation unit 106 calculates the NO concentration and the $NO_2$ concentration in the gas to be measured in which NO and $NO_2$ are mixed.

In step S9, the first gas sensor 10A determines whether or not there is a termination request (power off, maintenance, etc.) to terminate the measurement process of NO and $NO_2$. If there is not a termination request, the processes from step S1 and thereafter are repeated. In addition, in step S9, at a stage at which a termination request is made, the process of measuring NO and $NO_2$ in the first gas sensor 10A is brought to an end.

In the foregoing manner, the first gas sensor 10A acquires the sensor output under a condition (first condition) in which all of the $NO_2$ is converted into NO, without causing decomposition of the NO, and further acquires the sensor output under a condition (second condition) in which a portion of the $NO_2$ is converted into NO, without causing decomposition of the NO. In addition, the respective concentrations of NO and $NO_2$ are calculated on the basis of the first relational expression between the sensor output under the first condition, and the sensor output with respect to the NO concentration and the sensor output with respect to the $NO_2$ concentration under the first condition, and the second relational expression between the sensor output under the second condition, and the sensor output with respect to the NO concentration and the sensor output with respect to the $NO_2$ concentration under the second condition.

Consequently, it is possible to accurately measure the respective concentrations of a plurality of target components over a prolonged period, even under an atmosphere of a non-combusted component such as exhaust gas, and a plurality of target components (for example, NO and $NO_2$) that coexist in the presence of oxygen.

In addition, merely by changing the software of the control system of the first gas sensor 10A, the first gas sensor 10A is capable of easily realizing the process of measuring the concentrations of NO and $NO_2$ which heretofore could not be realized, without separately adding various measurement devices or the like as hardware. As a result, it is possible to improve the accuracy of controlling an NOx purification system and detecting failures thereof. In particular, it is possible to distinguish between NO and $NO_2$ in exhaust gas downstream of a DOC catalyst (Diesel Oxidation Catalyst), which contributes to detecting deterioration of the DOC catalyst.

Next, a gas sensor (hereinafter referred to as a second gas sensor 10B) according to a second embodiment will be described further with reference to FIGS. 8 and 9.

The second gas sensor 10B has substantially the same configuration as that of the first gas sensor 10A described above, but differs in terms of the configuration of the concentration calculation unit 106 thereof.

Figure 8:
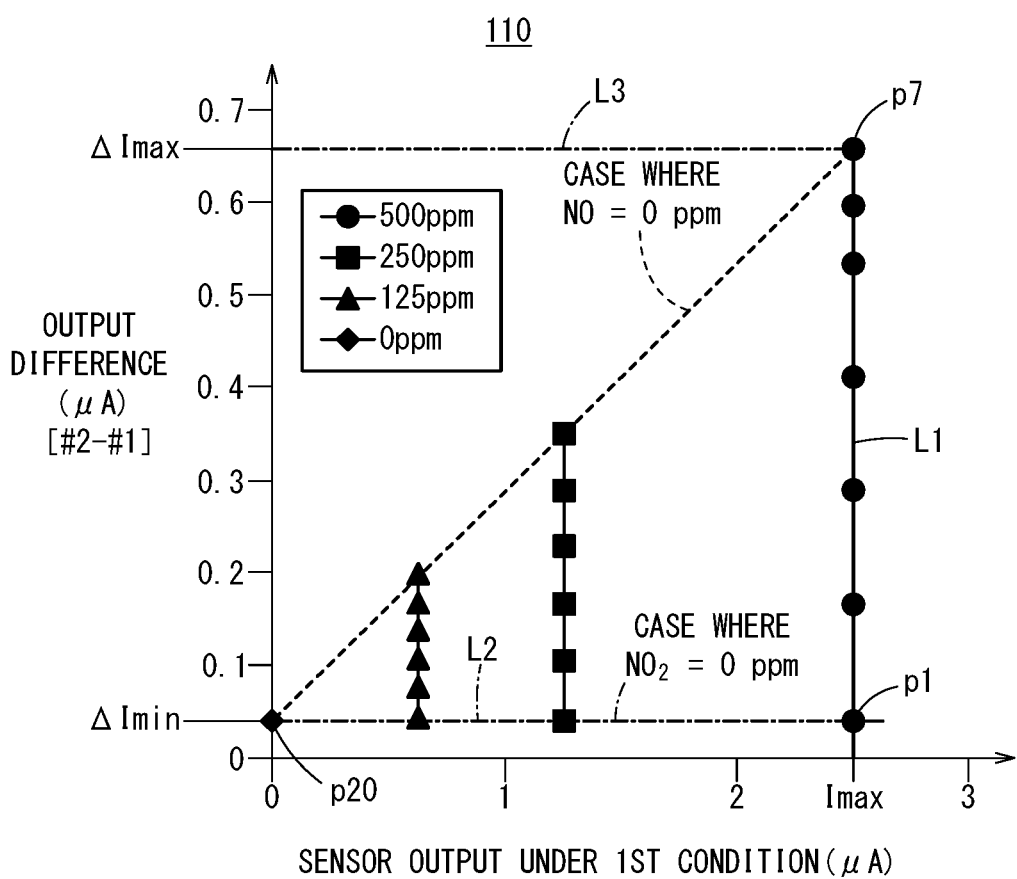
FIG. 8 is a graph showing a first map utilized by the second gas sensor.

More specifically, the concentration calculation unit 106 of the second gas sensor 10B determines the respective concentrations of NO and $NO_2$, on the basis of the sensor output under the first condition, an output difference obtained by subtracting the sensor output under the first condition from the sensor output under the second condition, and a first map 110 (see FIGS. 8 and 9).

The first map 110 is shown in the form of a graph, and is a graph in which, for example, as shown in FIG. 8, there is set on the horizontal axis the sensor output under the first condition, and on the vertical axis the output difference

[#2–#1] obtained by subtracting the sensor output under the first condition from the sensor output under the second condition.

In the first map 110, it is shown that points indicating concentrations (or a concentration ratio) of NO and $NO_2$ in the gas to be measured are present within a triangular region surrounded by three points p1, p7, and p20.

In FIG. 8, the point p1 is an intersecting point connecting a sensor output Imax (μA) (refer to line L1) under the first condition, and an output difference ΔImin (μA) (refer to line L2) obtained by subtracting the sensor output Imax (μA) under the first condition from the sensor output under the second condition, for a case in which $NO_2$ is 0 ppm, at an upper limit concentration (for example, a 500 ppm system) at which NO can be measured.

Similarly, the point p7 is an intersecting point connecting the sensor output Imax (μA) (refer to line L1) under the first condition, and the output difference ΔImin (μA) (refer to line L3) obtained by subtracting the sensor output Imax (μA) under the first condition from the sensor output under the second condition, for a case in which $NO_2$ is 500 ppm with NO being 0 ppm.

The point p20 is an intersecting point connecting the sensor output 0 (μA) (horizontal axis) under the first condition, and the output difference ΔImin (μA) obtained by subtracting the sensor output under the first condition from the sensor output under the second condition, for a case in which both NO and $NO_2$ are 0 ppm.

Furthermore, typically, in regards to a 500 ppm system, a 250 ppm system, and a 125 ppm system, for example, the first map 110 sets points at the same rate from the line L2, and allocates the NO concentrations and $NO_2$ concentrations to correspond to each of the points. When shown in the form of a table to facilitate understanding, the contents thereof are as shown in FIG. 9. These concentrations are obtained by experiment or by simulation.

By specifying points on the first map 110 from the sensor output under the first condition and the output difference [#2–#1], the NO concentration and the $NO_2$ concentration can be obtained. For example, at the point p1, the NO concentration is 500 ppm and the $NO_2$ concentration is 0 ppm, at the point p2, the NO concentration is 400 ppm and the $NO_2$ concentration is 111 ppm, and at the point p3, the NO concentration is 300 ppm and the $NO_2$ concentration is 222 ppm. If there is no corresponding point on the first map 110, the point nearest thereto may be specified, and the NO concentration and the $NO_2$ concentration may be obtained, for example, by a known type of approximation calculation.

Next, the process of measuring NO and $NO_2$ by the second gas sensor 10B will be described with reference to the flowchart of FIG. 10.

Figure 10:
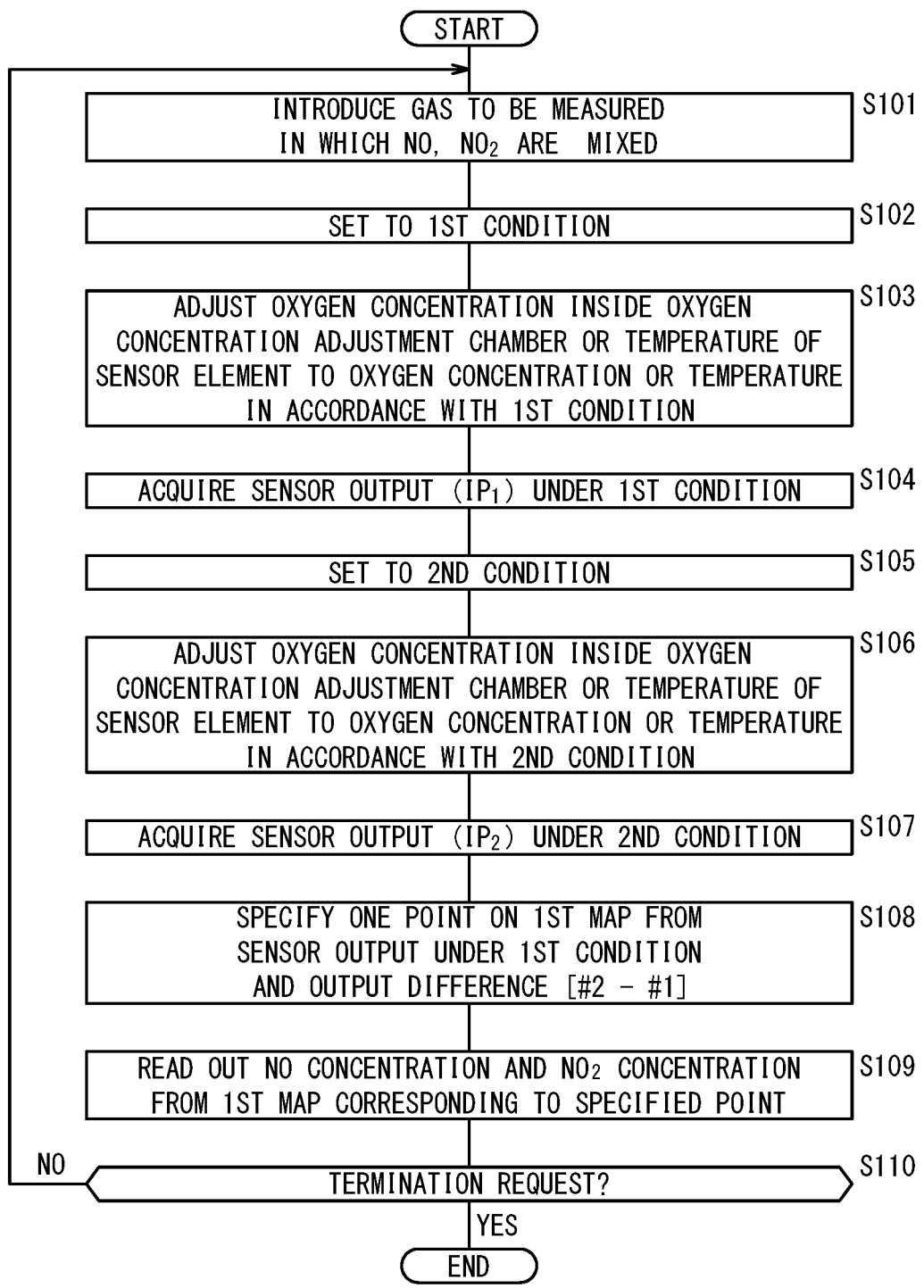
FIG. 10 is a flowchart showing a process of measuring NO and $NO_2$ by the second gas sensor.

First, steps S101 to S107 in FIG. 10 are the same as those of the above-described first gas sensor 10A (refer to steps S1 to S7 in FIG. 7), and therefore, duplicate descriptions of such steps will be omitted.

Thereafter, in step S108, the concentration calculation unit 106 specifies one point on the first map 110 from the sensor output under the first condition, and the output difference [#2–#1] obtained by subtracting the sensor output under the first condition from the sensor output under the second condition.

In step S109, the NO concentration and the $NO_2$ concentration corresponding to the specified point are read out from the first map 110, and at this time, the concentrations are set as the measured NO concentration and the measured $NO_2$ concentration. If there is no corresponding point on the first map 110, in the manner described above, the point nearest thereto is specified, and the NO concentration and the $NO_2$ concentration are obtained, for example, by a known type of approximation calculation.

In step S110, the second gas sensor 10B determines whether or not there is a termination request (power off, maintenance, etc.) to terminate the measurement process of NO and $NO_2$. If there is not a termination request, the processes from step S101 and thereafter are repeated. In addition, in step S110, at a stage at which a termination request is made, the process of measuring NO and $NO_2$ in the second gas sensor 10B is brought to an end.

The second gas sensor 10B also realizes the same effects as those of the above-described first gas sensor 10A. In particular, since it is sufficient to read the NO concentration and the $NO_2$ concentration from points specified on the first map 110, there is no need for a complicated calculation process, and the NO concentration and the $NO_2$ concentration can be acquired in a short period of time.

Next, a gas sensor (hereinafter referred to as a third gas sensor 10C) according to a third embodiment will be described with reference to FIG. 1, FIG. 2, and FIGS. 11A to 18.

The third gas sensor 10C has substantially the same configuration as that of the first gas sensor 10A described above, but differs therefrom in that it is possible to measure the respective concentrations of three target components, that is, NO, $NO_2$, and $NH_3$.

More specifically, in addition to the first condition and the second condition described above, a condition for partially decomposing NO, and for converting a portion of the $NH_3$ into NO is set as a third condition.

Next, a description will be given with reference to FIGS. 11A to 12 concerning the first condition through the third condition, with $NH_3$ being taken into consideration.

Figure 11A:
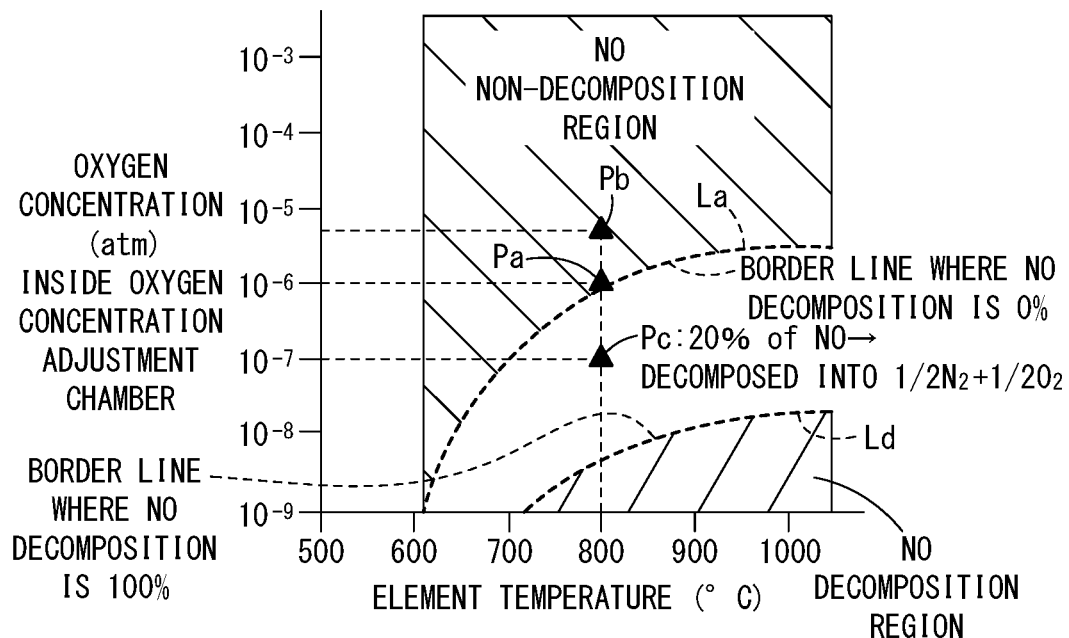
FIGS. 11A and 11B are diagrams showing oxygen concentration characteristics in an oxygen concentration adjustment chamber with respect to the temperature (element temperature) of a sensor element, and in particular.

FIG. 11A indicates a relationship between decomposition and non-decomposition of NO, in which there is shown on the vertical axis the oxygen concentration in the oxygen concentration adjustment chamber 18, and there is shown on the horizontal axis the temperature of the sensor element 12. In FIG. 11A, the dashed line La indicates a boundary line where a decomposition reaction of NO→(½)$N_2$+(½)$O_2$ is 0%, or in other words, where such a decomposition reaction does not occur. The dashed line Ld indicates a boundary line where the decomposition reaction takes place at 100%. Further, the plot Pa indicates an oxygen concentration and an element temperature corresponding to the first condition. The plot Pb indicates an oxygen concentration and an element temperature corresponding to the second condition. The plot Pc indicates an oxygen concentration and an element temperature corresponding to the third condition. From FIG. 11A, it can be understood that in the first condition and the second condition, the NO decomposition reaction does not proceed, however, in the third condition, among the NO, 20% thereof undergoes decomposition according to the reaction NO→(½)$N_2$+(½)$O_2$.

Figure 11B:
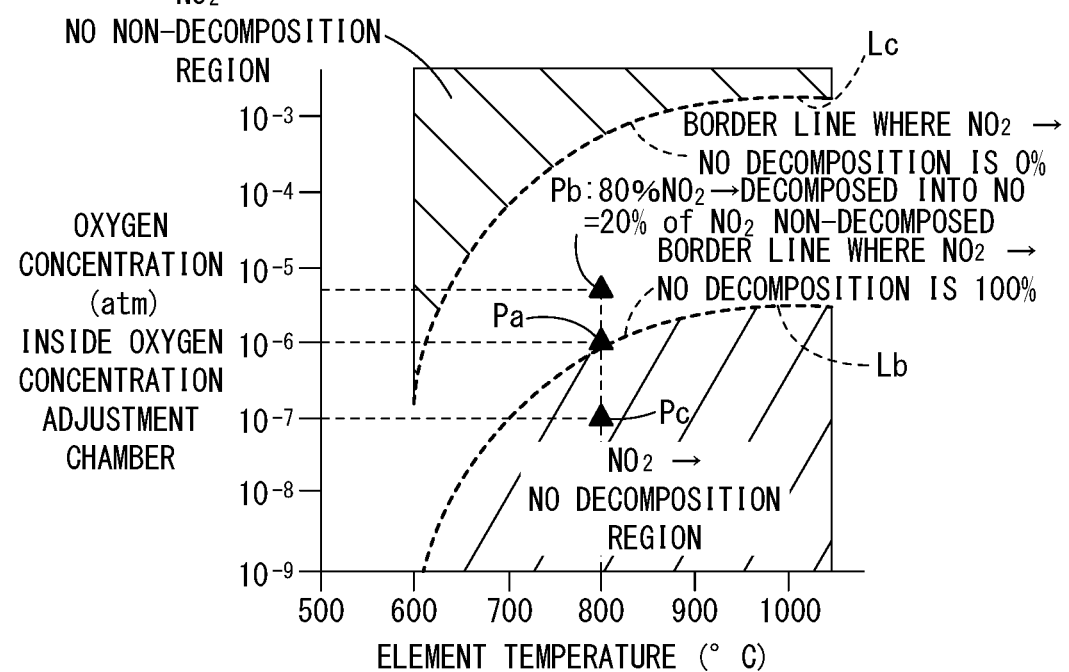

Similarly, FIG. 11B indicates a relationship between decomposition and non-decomposition of $NO_2$, in which there is shown on the vertical axis the oxygen concentration in the oxygen concentration adjustment chamber 18, and there is shown on the horizontal axis the temperature of the sensor element 12. In FIG. 11B, the dashed line Lc indicates a boundary line where a decomposition reaction of $NO_2$→NO+(½)$O_2$ is 0%, or in other words, where such a decomposition reaction does not occur. The dashed line Lb indicates a boundary line where the decomposition reaction takes place at 100%. Further, the plot Pa indicates an oxygen concentration and an element temperature corresponding to the first condition. The plot Pb indicates an oxygen concentration and an element temperature corresponding to the second condition. The plot Pc indicates an oxygen concentration and an element temperature corresponding to the third condition. From FIG. 11B, it can be understood that in the first condition and the third condition, the $NO_2$ decomposition reaction proceeds at 100%, however, in the second condition, among the $NO_2$, 20% thereof does not undergo decomposition.

Figure 12:
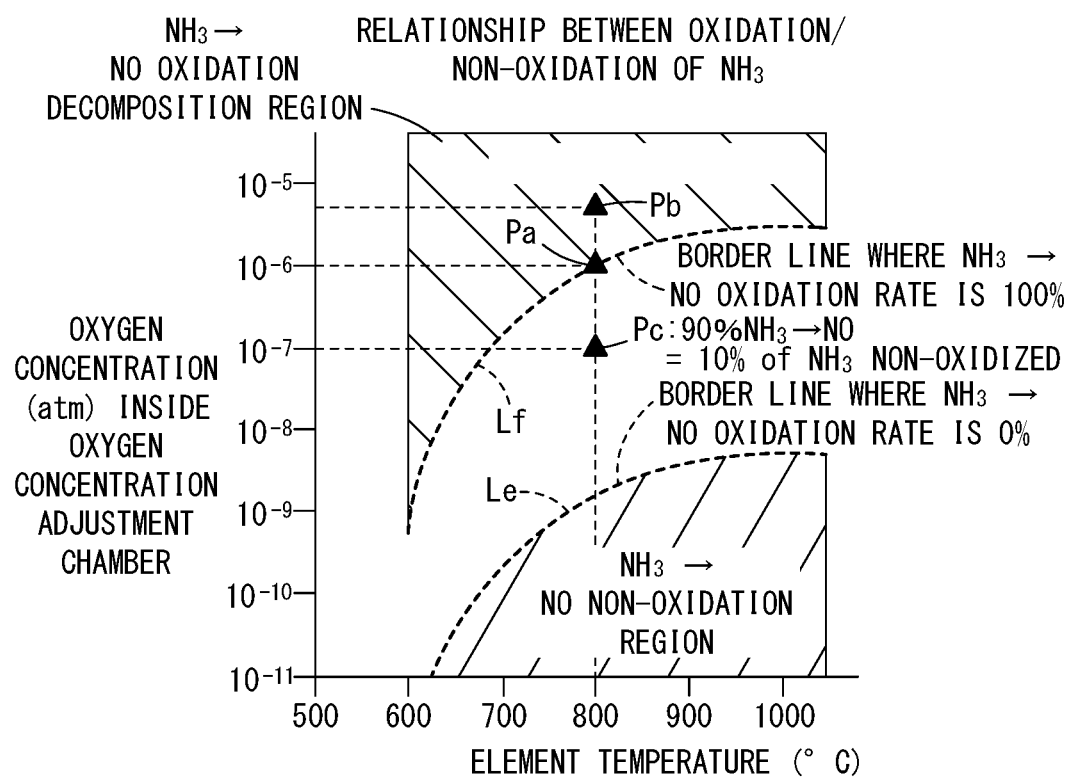
FIG. 12 is a diagram showing oxygen concentration characteristics in the oxygen concentration adjustment chamber with respect to the temperature (element temperature) of the sensor element, and in particular, a relationship between decomposition and non-decomposition of $NH_3$.

FIG. 12 indicates a relationship between decomposition and non-decomposition of $NH_3$, in which there is shown on the vertical axis the oxygen concentration in the oxygen concentration adjustment chamber 18, and there is shown on the horizontal axis the temperature of the sensor element 12. In FIG. 12, the dashed line Le indicates a boundary line where an oxidation reaction of $4NH_3+5O_2 \rightarrow 4NO+6H_2O$ is 0%, or in other words, where such an oxidation reaction does not occur. The dashed line Lf indicates a boundary line where the oxidation reaction takes place at 100%. Further, the plot Pa indicates an oxygen concentration and an element temperature corresponding to the first condition. The plot Pb indicates an oxygen concentration and an element temperature corresponding to the second condition. The plot Pc indicates an oxygen concentration and an element temperature corresponding to the third condition. From FIG. 12, it can be understood that in the first condition and the second condition, the $NH_3$ oxidation reaction proceeds at 100%, however, in the third condition, among the $NH_3$, 10% thereof does not undergo decomposition.

Moreover, in FIG. 12, the boundary line where the $NH_3$ oxidation rate is 100% and the boundary line where the $NH_3$ oxidation rate is 0% are not indicative of the absolute progress of the oxidation reaction. For example, considering the boundary line where the $NH_3$ oxidation rate is 100%, a combination of the oxygen concentration of the oxygen concentration adjustment chamber 18 and the temperature of the measurement element is shown in which, even if the oxygen concentration in the oxygen concentration adjustment chamber 18 increases more than such a value, the slope (i.e., sensitivity coefficient) of the pump current $IP_2$ flowing to the measurement pump cell 61 that is arranged in the measurement chamber 20 with respect to the $NH_3$ concentration does not increase. Considering the boundary line where the $NH_3$ oxidation rate is 0%, a combination of the oxygen concentration of the oxygen concentration adjustment chamber 18 and the temperature of the measurement element is shown in which the pump current $IP_2$ flowing to the measurement pump cell 61 with respect to the $NH_3$ concentration in the gas to be measured flows in the direction of pumping oxygen into the measurement chamber 20. In order to change the boundary lines depending on the catalytic activity of the main interior side pump electrode 42 that is disposed inside the oxygen concentration adjustment chamber 18, and the microstructure of the electrode, experimental confirmations should be made for each of the element temperature, the electrode material, and the electrode microstructure.

The change from the first condition to the third condition according to the third embodiment is carried out, for example, by changing the oxygen concentration in the oxygen concentration adjustment chamber 18 while keeping the temperature constant. However, the measurement conditions can be arbitrarily set insofar as they do not deviate from a concept in which "by changing the setting conditions of the oxygen concentration and the temperature of the oxygen concentration adjustment chamber from the reference conditions, a change is made to the chemical equilibrium of the target components (NO, $NO_2$, $NH_3$) occurring in the oxygen concentration adjustment chamber, the sensor outputs obtained in the measurement chamber are intentionally changed, and the respective component concentrations are obtained from the sensor outputs under the reference conditions and the changed amount of the sensor outputs due to the change in the conditions," which is the basic concept of the present invention. For example, the oxygen concentration in the oxygen concentration adjustment chamber 18 is kept constant while the temperature is changed, and the like.

Figure 13:
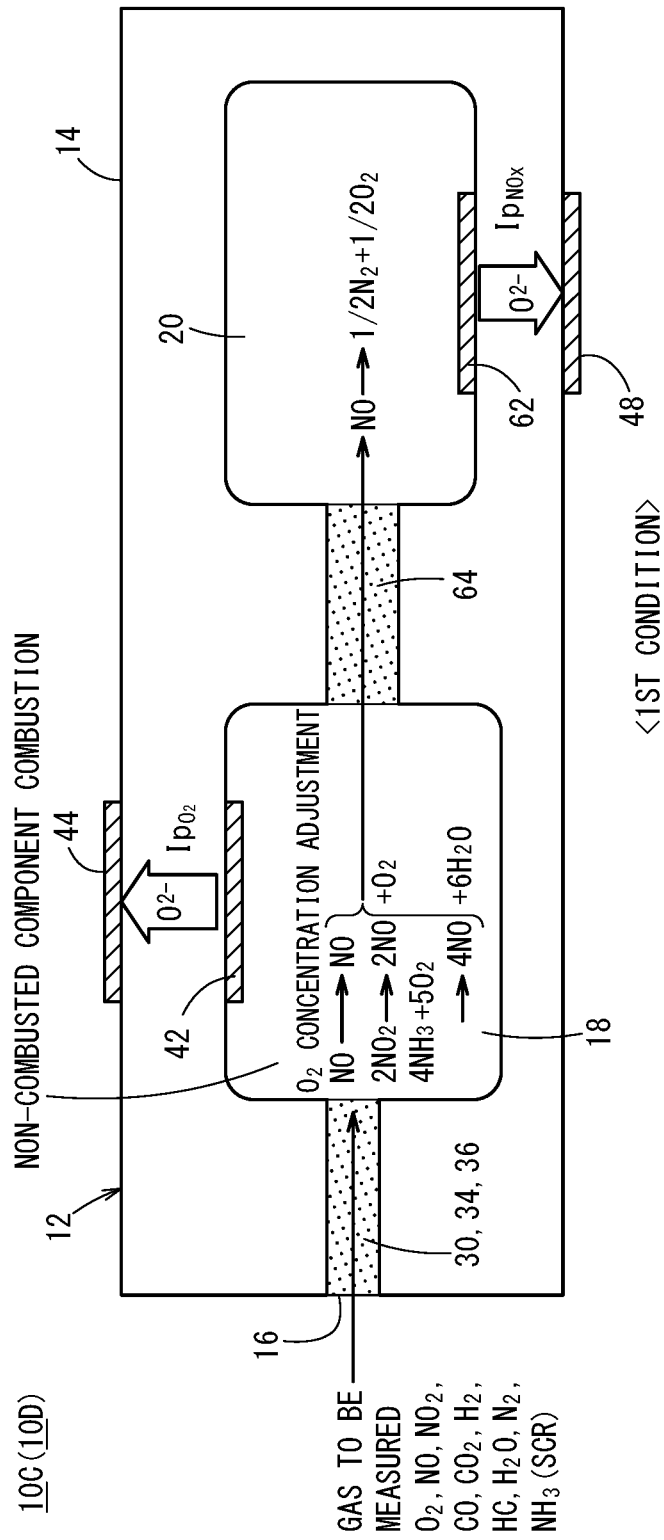
FIG. 13 is an explanatory diagram schematically showing a reaction in an oxygen concentration adjustment chamber and a reaction in a measurement chamber under a first condition, in a third gas sensor and a fourth gas sensor.

The reaction inside the oxygen concentration adjustment chamber 18 and the reaction inside the measurement chamber 20 will be briefly described with reference to the schematic views shown in FIGS. 13 to 15. First, in the case of being set to the first condition, as shown in FIG. 13, NO is not decomposed inside the oxygen concentration adjustment chamber 18, but remains as is in the form of NO. In regards to $NO_2$, a decomposition reaction of $2NO_2 \rightarrow 2NO+O_2$ occurs. In regards to $NH_3$, the $NH_3$ is oxidized into NO by an oxidation reaction of $4NH_3+5O_2 \rightarrow 4NO+6H_2O$. Accordingly, NO enters into the measurement chamber 20 from the oxygen concentration adjustment chamber 18, whereas $NO_2$ and $NH_3$ do not enter therein. Inside the measurement chamber 20, a decomposition reaction of $NO \rightarrow (1/2)N_2+(1/2)O_2$ occurs, and among the products of the reaction, in accordance with the $O_2$ being pumped out, it is detected as a sensor output (pump current $IP_2$).

Figure 14:
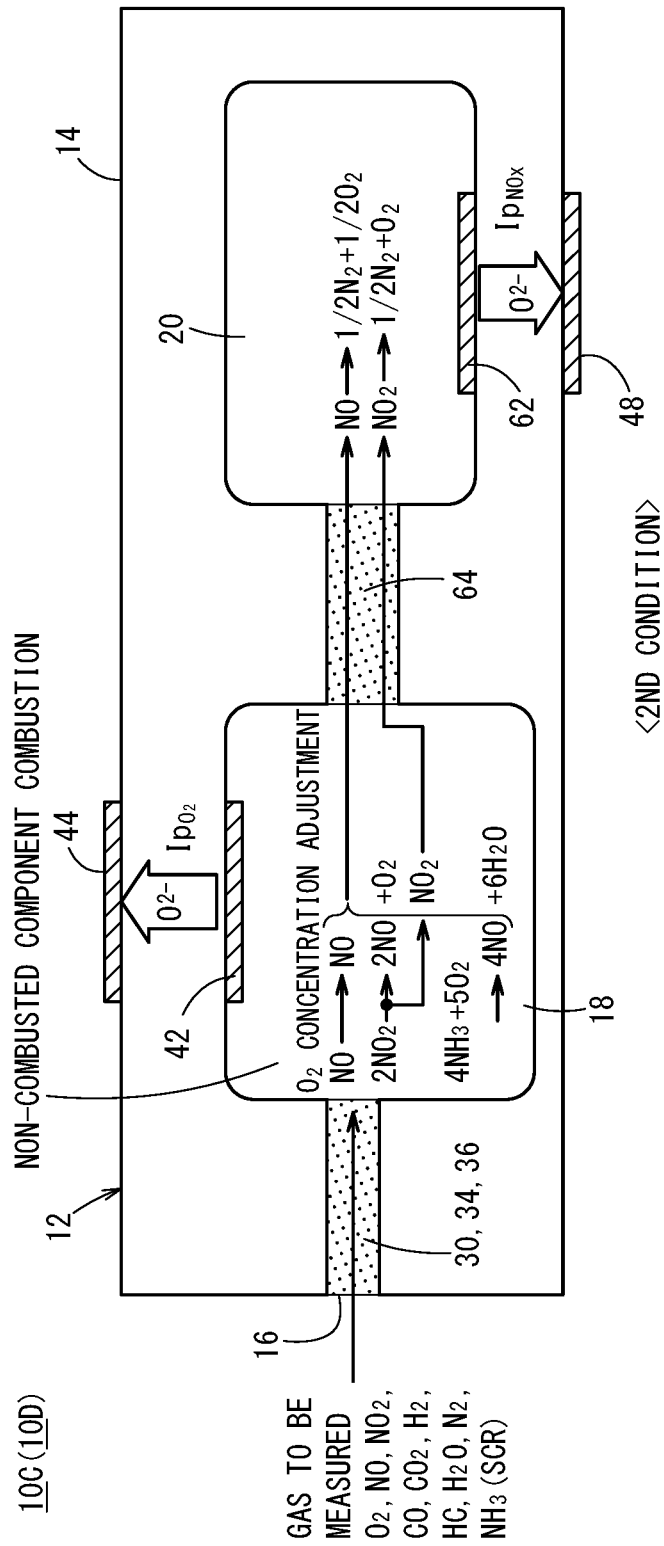
FIG. 14 is an explanatory diagram schematically showing a reaction in an oxygen concentration adjustment chamber and a reaction in a measurement chamber under a second condition, in the third gas sensor and the fourth gas sensor.

In the case of being set to the second condition, as shown in FIG. 14, NO is not decomposed inside the oxygen concentration adjustment chamber 18, but remains as is in the form of NO. In regards to $NO_2$, for example, 80% of the $NO_2$ is decomposed into NO by a decomposition reaction of $2NO_2 \rightarrow 2NO+O_2$, and the remaining 20% of the $NO_2$ is not decomposed. In regards to $NH_3$, the $NH_3$ is oxidized into NO by an oxidation reaction of $4NH_3+5O_2 \rightarrow 4NO+6H_2O$. Accordingly, NO and $NO_2$ enter into the measurement chamber 20 from the oxygen concentration adjustment chamber 18. Inside the measurement chamber 20, a decomposition reaction of $NO \rightarrow (1/2)N_2+(1/2)O_2$, and a decomposition reaction of $NO_2 (1/2)N_2+O_2$ occur. Among the products of the reactions, in accordance with the $O_2$ being pumped out, it is detected as a sensor output (pump current $IP_2$). In this case, excessive oxygen ions are brought in by the $NO_2$ which has entered into the measurement chamber 20, and the sensor output becomes larger in comparison with the first condition and the third condition.

Figure 15:
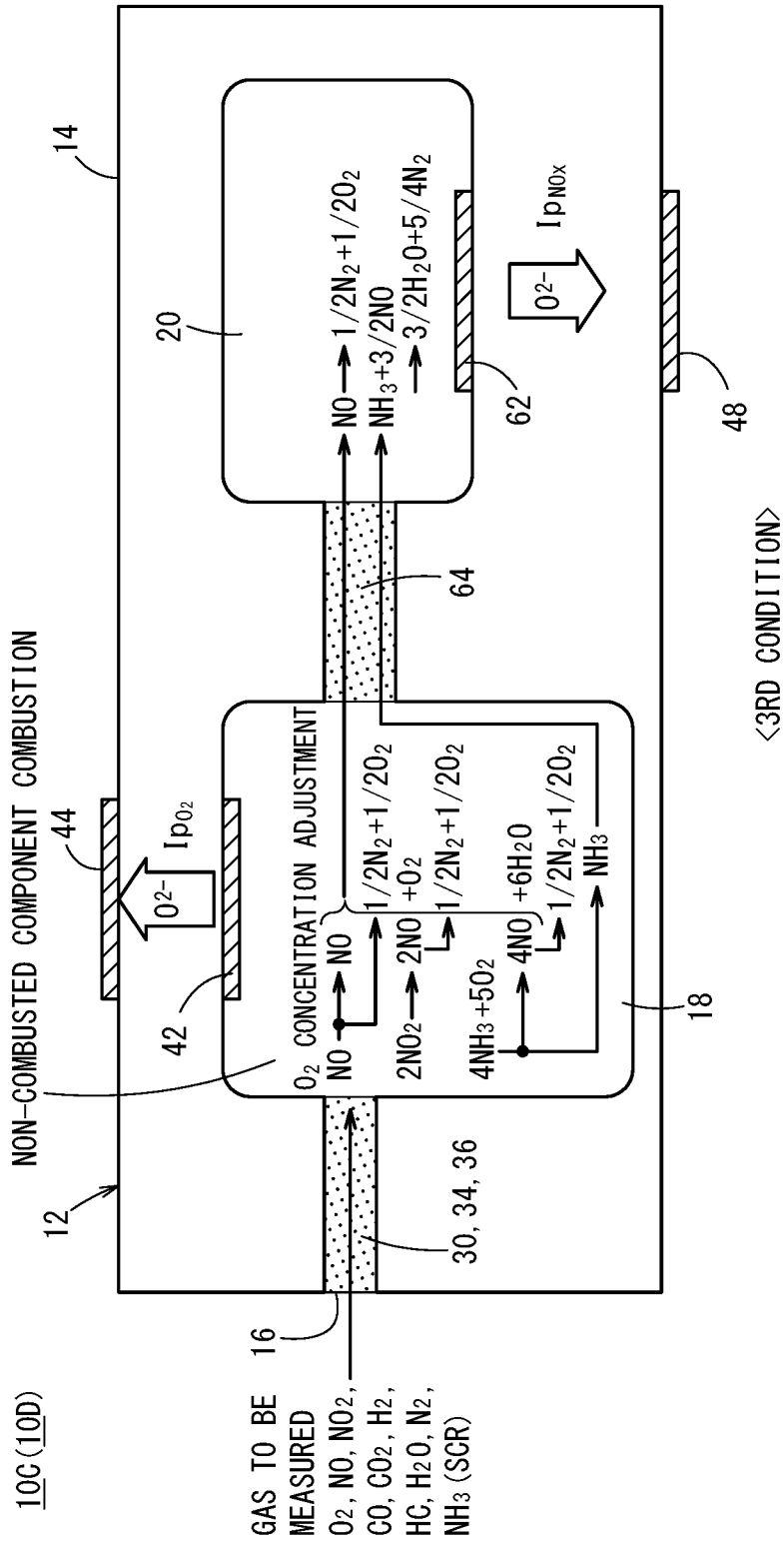
FIG. 15 is an explanatory diagram schematically showing a reaction in an oxygen concentration adjustment chamber and a reaction in a measurement chamber under a third condition, in the third gas sensor and the fourth gas sensor.

In the case of being set to the third condition, as shown in FIG. 15, in regards to NO, for example, 20% of the NO is decomposed inside the oxygen concentration adjustment chamber 18 by the decomposition reaction of $(1/2)N_2+(1/2)O_2$, whereas the remaining 80% of the NO is not decomposed. In regards to $NO_2$, a decomposition reaction of $2NO_2 \rightarrow 2NO+O_2$ occurs, and together therewith, 20% of the NO produced in the decomposition reaction is also decomposed by a decomposition reaction of $(1/2)N_2+(1/2)O_2$. In regards to $NH_3$, for example, 90% of the $NH_3$ is oxidized into NO by an oxidation reaction of $4NH_3+5O_2 \rightarrow 4NO+6H_2O$, and the remaining 10% of the $NH_3$ is not oxidized. In this case as well, 20% of the NO produced by the oxidation reaction is decomposed by the decomposition reaction of $(1/2)N_2+(1/2)O_2$. Accordingly, NO and $NH_3$ enter into the measurement chamber 20 from the oxygen concentration adjustment chamber 18. Inside the measurement chamber 20, a decomposition reaction of $NO \rightarrow (1/2)N_2+(1/2)O_2$, and a decomposition reaction of $NH_3+(3/2)NO \rightarrow (3/2)H_2O+(5/4)N_2$ occur. In this case, the NO inside the measurement chamber 20 is consumed by the decomposition of $NH_3$, and the sensor output is lower in comparison with the first condition and the second condition.

Figure 16A:
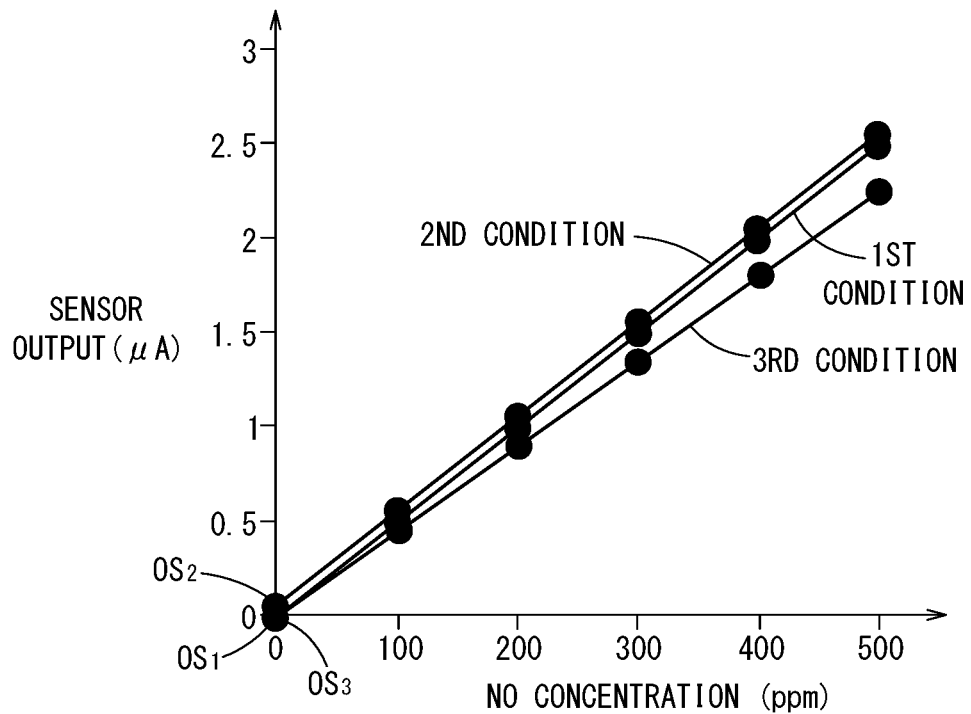
FIG. 16A is a graph showing sensor output characteristics with respect to NO concentration under the first condition, sensor output characteristics with respect to NO concentration under the second condition, and sensor output characteristics with respect to NO concentration under the third condition.

As shown in FIG. 16A, in the case of only NO being introduced under the first condition, when the NO concentration is 0 ppm, in the sensor output with respect to the NO concentration, an offset current $OS_1$ appears originating from the oxygen concentration inside the oxygen concentration adjustment chamber 18 under the first condition. In addition, as the NO concentration rises, the sensor output also rises proportionally.

Figure 16B:
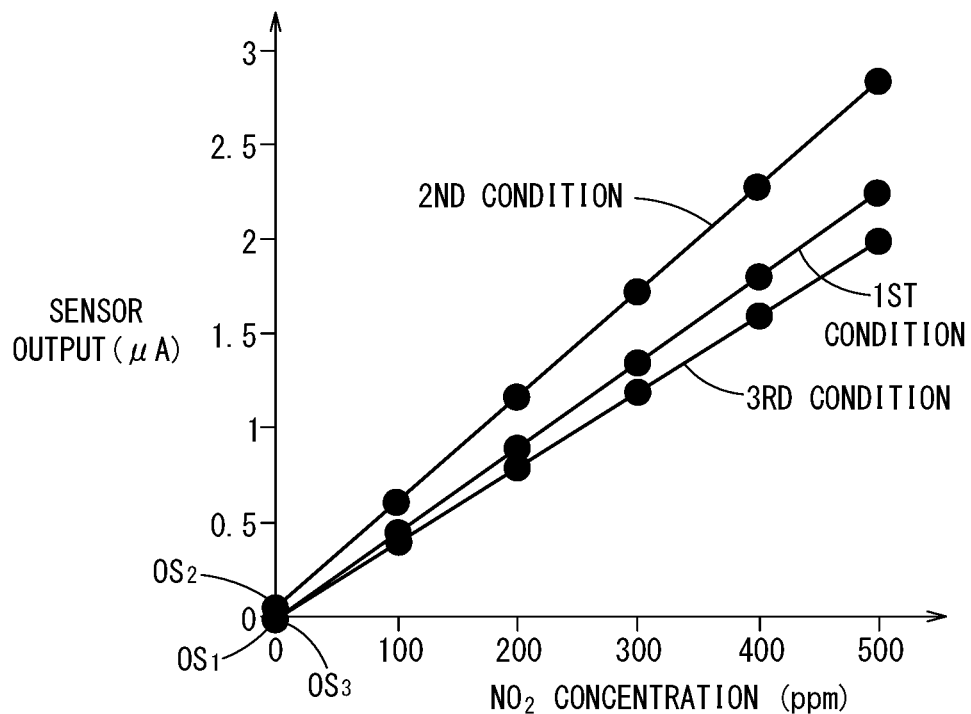
FIG. 16B is a graph showing sensor output characteristics with respect to $NO_2$ concentration under the first condition, sensor output characteristics with respect to $NO_2$ concentration under the second condition, and sensor output characteristics with respect to $NO_2$ concentration under the third condition.

As shown in FIG. 16B, in the case of only $NO_2$ being introduced under the first condition, when the $NO_2$ concentration is 0 ppm, in the sensor output with respect to the $NO_2$ concentration, an offset current $OS_1$ appears originating from the oxygen concentration inside the oxygen concentration adjustment chamber 18 under the first condition. Additionally, as the $NO_2$ concentration rises, the sensor output also rises proportionally, however, the slope thereof is smaller than the slope of the NO concentration under the first condition, due to the difference between the diffusion coefficients of NO and $NO_2$. When the slope of the NO concentration under the first condition is 1, the slope thereof is about 0.9.

Figure 17:
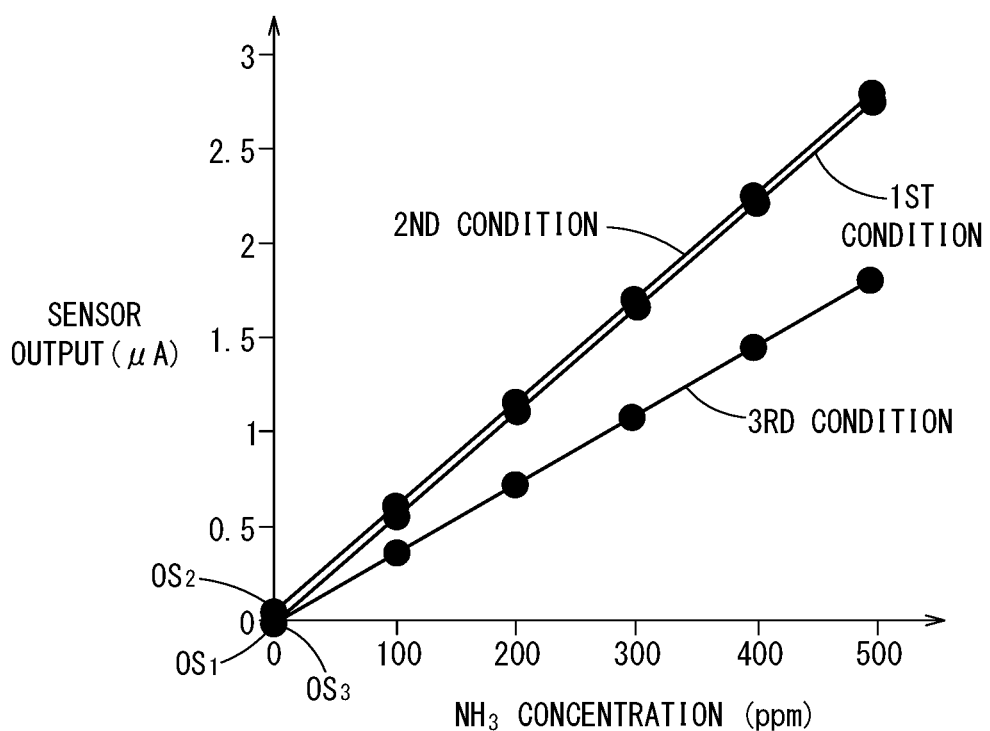
FIG. 17 is a graph showing sensor output characteristics with respect to $NH_3$ concentration under the first condition, sensor output characteristics with respect to $NH_3$ concentration under the second condition, and sensor output characteristics with respect to $NH_3$ concentration under the third condition.

As shown in FIG. 17, in the case of only $NH_3$ being introduced under the first condition, when the $NH_3$ concentration is 0 ppm, in the sensor output with respect to the $NH_3$ concentration, an offset current $OS_1$ appears originating from the oxygen concentration inside the oxygen concentration adjustment chamber 18 under the first condition. Additionally, as the $NH_3$ concentration rises, the sensor output also rises proportionally, however, the slope thereof is greater than the slope of the NO concentration under the first condition. When the slope of the NO concentration under the first condition is 1, the slope thereof is about 1.1.

Accordingly, a third relational expression (3) between the sensor output $IP_1$ under the first condition, the sensor output (NO) corresponding to the NO concentration, the sensor output ($NO_2$) corresponding to the $NO_2$ concentration, and the sensor output ($NH_3$) corresponding to the $NH_3$ concentration under the first condition is expressed in the following manner.

$$IP_1=NO+0.9NO_2+1.1NH_3+OS_1 \quad (3)$$

Similarly, as shown in FIG. 16A, in the case of only NO being introduced under the second condition, when the NO concentration is 0 ppm, in the sensor output with respect to the NO concentration, an offset current $OS_2$ appears originating from the oxygen concentration inside the oxygen concentration adjustment chamber 18 under the second condition. In addition, as the NO concentration rises, the sensor output also rises proportionally. From the fact that only NO is introduced, the slope of the NO concentration is the same as in the case of the first condition.

As shown in FIG. 16B, in the case of only $NO_2$ being introduced under the second condition, when the $NO_2$ concentration is 0 ppm, in the sensor output with respect to the $NO_2$ concentration, an offset current $OS_2$ appears originating from the oxygen concentration inside the oxygen concentration adjustment chamber 18 under the second condition. Additionally, as the $NO_2$ concentration rises, the sensor output also rises proportionally, however, the slope thereof is greater than the slope of the NO concentration under the first condition. This is because the $NO_2$, which has arrived at the measurement chamber 20 without being decomposed, is then decomposed, whereby the amount of $O_2$ becomes greater than the amount at which NO is decomposed. When the slope of the NO concentration under the second condition is 1, the slope thereof is about 1.12.

As shown in FIG. 17, in the case of only $NH_3$ being introduced under the second condition, when the $NH_3$ concentration is 0 ppm, in the sensor output with respect to the $NH_3$ concentration, an offset current $OS_2$ appears originating from the oxygen concentration inside the oxygen concentration adjustment chamber 18 under the second condition. Additionally, as the $NH_3$ concentration rises, the sensor output also rises proportionally, however, the slope thereof is greater than the slope of the NO concentration under the first condition. When the slope of the NO concentration under the first condition is 1, the slope thereof is about 1.1.

Accordingly, a fourth relational expression (4) between the sensor output $IP_2$ under the second condition, the sensor output (NO) corresponding to the NO concentration, the sensor output ($NO_2$) corresponding to the $NO_2$ concentration, and the sensor output ($NH_3$) corresponding to the $NH_3$ concentration under the second condition is expressed in the following manner.

$$IP_2=NO+1.12NO_2+1.1NH_3+OS_2 \quad (4)$$

Similarly, in the case of only NO being introduced under the third condition, when the NO concentration is 0 ppm, as shown in FIG. 16A, in the sensor output with respect to the NO concentration, an offset current $OS_3$ appears originating from the oxygen concentration inside the oxygen concentration adjustment chamber 18 under the third condition. Additionally, as the NO concentration rises, the sensor output also rises proportionally, however, the slope thereof is smaller than the slope of the NO concentration under the first condition. This is because 10% of the NO is decomposed inside the oxygen concentration adjustment chamber 18. When the slope of the NO concentration under the first condition is 1, the slope thereof is about 0.9.

In the case of only $NO_2$ being introduced under the third condition, when the $NO_2$ concentration is 0 ppm, as shown in FIG. 16B, in the sensor output with respect to the $NO_2$ concentration, an offset current $OS_3$ appears originating from the oxygen concentration inside the oxygen concentration adjustment chamber 18 under the third condition. Additionally, as the $NO_2$ concentration rises, the sensor output also rises proportionally, however, the slope thereof is smaller than the slope of the NO concentration under the first condition, due to the difference between the diffusion coefficients of NO and $NO_2$, and the fact that 10% of the NO undergoes decomposition inside the oxygen concentration adjustment chamber 18. When the slope of the NO concentration under the first condition is 1, the slope thereof is about 0.8.

In the case of only $NH_3$ being introduced under the third condition, when the $NH_3$ concentration is 0 ppm, as shown in FIG. 17, in the sensor output with respect to the $NH_3$ concentration, an offset current $OS_3$ appears originating from the oxygen concentration inside the oxygen concentration adjustment chamber 18 under the third condition. Additionally, as the $NH_3$ concentration rises, the sensor output also rises proportionally, however, the slope thereof is smaller than the slope of the NO concentration under the first condition. When the slope of the NO concentration under the first condition is 1, the slope thereof is about 0.72.

Accordingly, a fifth relational expression (5) between the sensor output $IP_3$ under the third condition, the sensor output (NO) corresponding to the NO concentration, the sensor output ($NO_2$) corresponding to the $NO_2$ concentration, and the sensor output ($NH_3$) corresponding to the $NH_3$ concentration under the third condition is expressed in the following manner.

$$IP_3 = 0.9NO + 0.8NO_2 + 0.72NH_3 + OS_3 \quad (5)$$

From the fact that all of the offset currents $OS_1$, $OS_2$, and $OS_3$ are constants, by simultaneously solving the trinomial equations of the third relational expression (3), the fourth relational expression (4), and the fifth relational expression (5), it is possible to calculate the NO concentration, the $NO_2$ concentration, and the $NH_3$ concentration in the gas to be measured in which NO, $NO_2$, and $NH_3$ are mixed.

Next, the process of measuring NO, $NO_2$, and $NH_3$ by the third gas sensor 10C will be described with reference to the flowchart of FIG. 18.

Figure 18:
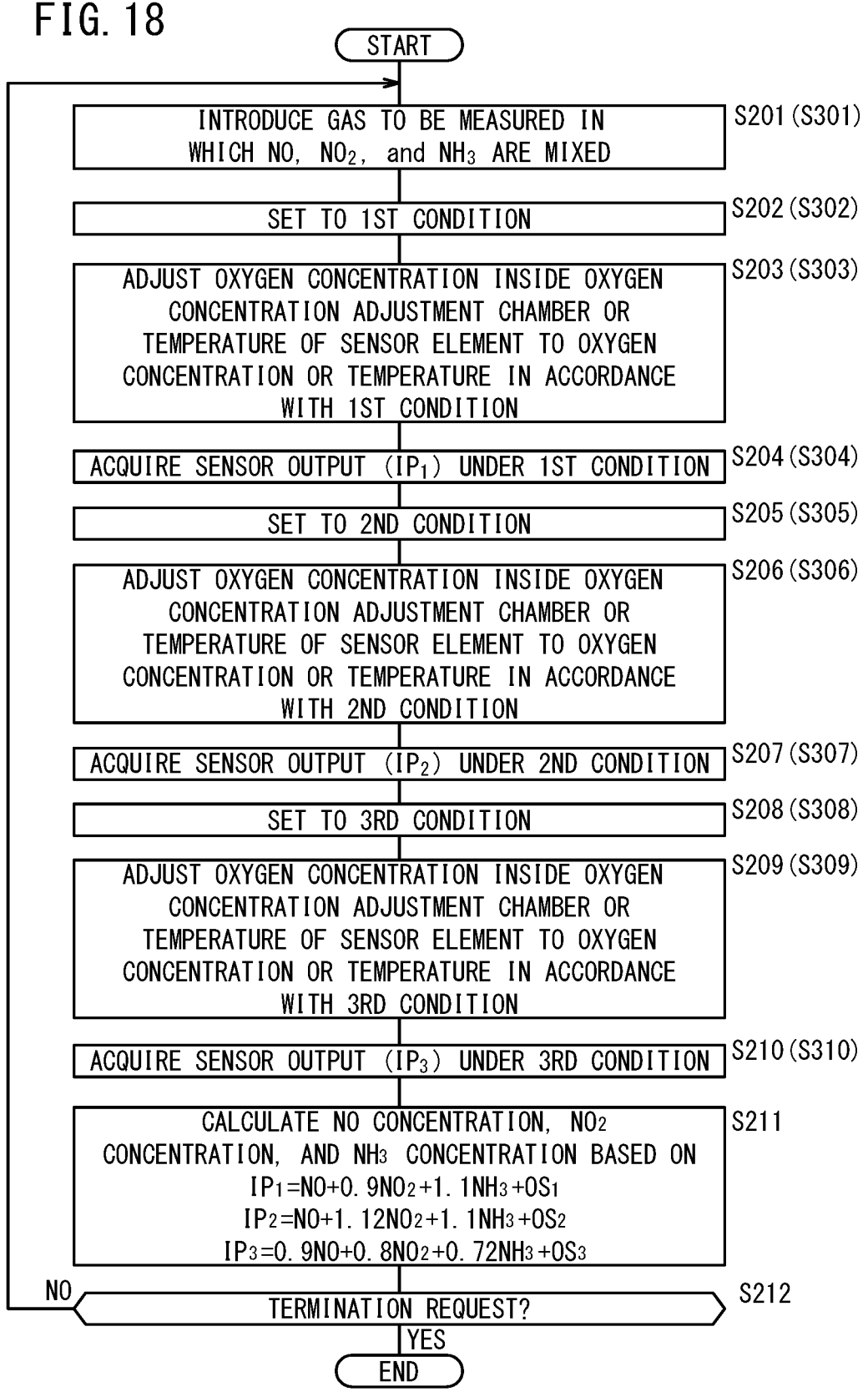
FIG. 18 is a flowchart showing a process of measuring NO, $NO_2$, and $NH_3$ by the third gas sensor.

First, in step S201 of FIG. 18, the third gas sensor 10C introduces a gas to be measured in which NO, $NO_2$, and $NH_3$ are mixed into the oxygen concentration adjustment chamber 18 through the gas introduction port 16.

In step S202, the condition setting unit 104 sets the first condition, and activates the oxygen concentration control unit 100 or the temperature control unit 102.

In step S203, the oxygen concentration control unit 100 or the temperature control unit 102 adjusts the oxygen concentration inside the oxygen concentration adjustment chamber 18 or the temperature of the sensor element 12 to an oxygen concentration or a sensor temperature in accordance with the first condition.

In step S204, the concentration calculation unit 106 acquires the sensor output ($IP_1$) under the first condition.

In step S205, the condition setting unit 104 sets the second condition, and activates the oxygen concentration control unit 100 or the temperature control unit 102.

In step S206, the oxygen concentration control unit 100 or the temperature control unit 102 adjusts the oxygen concentration inside the oxygen concentration adjustment chamber 18 or the temperature of the sensor element 12 to an oxygen concentration or a sensor temperature in accordance with the second condition.

In step S207, the concentration calculation unit 106 acquires the sensor output ($IP_2$) under the second condition.

In step S208, the condition setting unit 104 sets the third condition, and activates the oxygen concentration control unit 100 or the temperature control unit 102.

In step S209, the oxygen concentration control unit 100 or the temperature control unit 102 adjusts the oxygen concentration inside the oxygen concentration adjustment chamber 18 or the temperature of the sensor element 12 to an oxygen concentration or a sensor temperature in accordance with the third condition.

In step S210, the concentration calculation unit 106 acquires the sensor output ($IP_3$) under the third condition.

In step S211, by simultaneously solving the trinomial equations of the third relational expression (3), the fourth relational expression (4), and the fifth relational expression (5), the concentration calculation unit 106 calculates the NO concentration, the $NO_2$ concentration, and the $NH_3$ concentration in the gas to be measured in which NO, $NO_2$, and $NH_3$ are mixed.

In step S212, the third gas sensor 10C determines whether or not there is a termination request (power off, maintenance, etc.) to terminate the measurement process of NO, $NO_2$, and $NH_3$. If there is not a termination request, the processes from step S201 and thereafter are repeated. In addition, in step S212, at a stage at which a termination request is made, the process of measuring NO, $NO_2$, and $NH_3$ in the third gas sensor 10C is brought to an end.

In the foregoing manner, the third gas sensor 10C acquires the sensor output under a condition (first condition) in which all of the $NO_2$ is converted into NO, without causing decomposition of the NO, and further acquires the sensor output under a condition (second condition) in which a portion of the $NO_2$ is converted into NO, without causing decomposition of the NO, and sets as a third condition a condition for converting a portion of the $NH_3$ into NO, while causing decomposition of a portion of the NO. Then, the concentrations of NO, $NO_2$, and $NH_3$ are calculated on the basis of the third relational expression, the fourth relational expression, and the fifth relational expression described above.

Consequently, it is possible to accurately measure the respective concentrations of a plurality of target components over a prolonged period, even under an atmosphere of a non-combusted component such as exhaust gas, and a plurality of target components (for example, NO, $NO_2$, and $NH_3$) that coexist in the presence of oxygen.

In addition, merely by changing the software of the control system of the third gas sensor 10C, the third gas sensor 10C is made capable of easily realizing the process of measuring the concentrations of NO, $NO_2$, and $NH_3$ which heretofore could not be realized, without separately adding various measurement devices or the like as hardware. As a result, it is possible to improve the accuracy of controlling an NOx purification system and detecting failures thereof. In particular, it is possible to distinguish between NO and $NO_2$ in exhaust gas downstream of a DOC catalyst, which contributes to detecting deterioration of the DOC catalyst. In addition, it is also possible to distinguish between NO, $NO_2$, and $NH_3$ in exhaust gas downstream of an SCR system, which contributes to precisely controlling the injected amount of urea, as well as detecting deterioration of the SCR system.

Next, a gas sensor (hereinafter referred to as a fourth gas sensor 10D) according to a fourth embodiment will be described further with reference to FIGS. 19 and 20.

The fourth gas sensor 10D has substantially the same configuration as that of the third gas sensor 10C described above, but differs in terms of the configuration of the concentration calculation unit 106 thereof.

More specifically, the concentration calculation unit 106 of the fourth gas sensor 10D determines the respective concentrations of NO, $NO_2$, and $NH_3$, on the basis of the sensor output under the first condition, a first output difference [#2–#1] obtained by subtracting the sensor output under the first condition from the sensor output under the second condition, a second output difference [#3–#2] obtained by subtracting the sensor output under the second condition from the sensor output under the third condition, and a second map 112.

Figure 19:
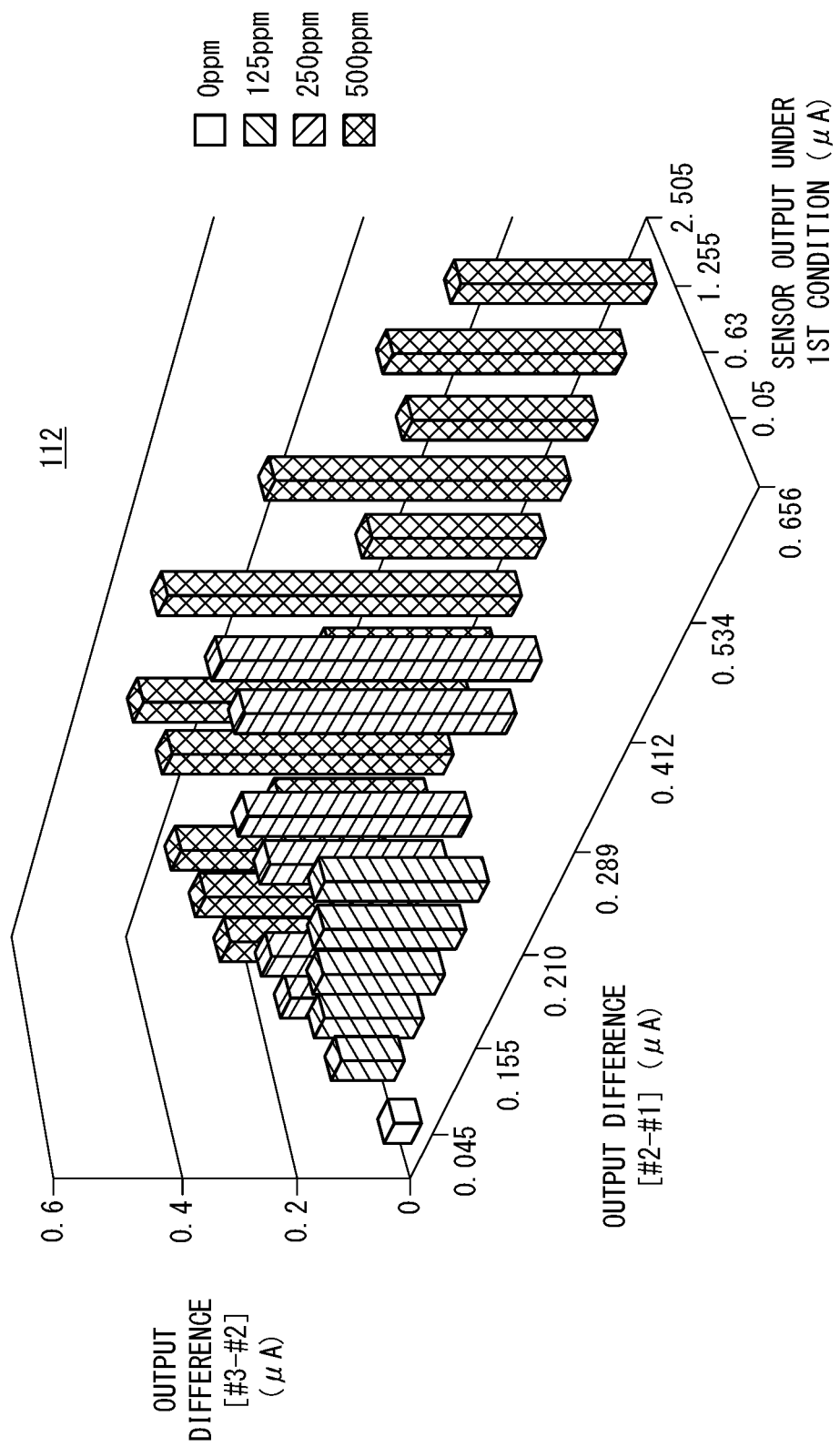
FIG. 19 is a graph showing a second map utilized by the fourth gas sensor.

The second map 112 is shown in the form of a graph, and is a graph in which, for example, as shown in FIG. 19, there is set on the x-axis the sensor output under the first condition, there is set on the y-axis perpendicular to the x-axis the first output difference [#2–#1], and there is set on the z-axis perpendicular to both the x-axis and the y-axis the second output difference [#3–#2].

In addition, in the second map 112, a plurality of points are set, and the NO concentration, the $NO_2$ concentration, and the $NH_3$ concentration are allocated with respect to each of such points. When shown in the form of a table to facilitate understanding, the contents thereof are as shown in FIG. 20. In FIG. 20, only a 500 ppm system is shown representatively. These concentrations are obtained by experiment or by simulation. Since this second map 112 has a three-dimensional structure (refer to FIG. 19), one point is specified by the sensor output under the first condition, the first output difference [#2–#1], and the second output difference [#3–#2]. By reading out from the second map 112 the NO concentration, the $NO_2$ concentration, and the $NH_3$ concentration corresponding to such a point, the NO concentration, the $NO_2$ concentration, and the $NH_3$ concentration can be obtained.

For example, at the point p1, the NO concentration is 500 ppm, the $NO_2$ concentration is 0 ppm, and the $NH_3$ concentration is 0 ppm, at the point p10, the NO concentration is 300 ppm, the $NO_2$ concentration is 222 ppm, and the $NH_3$ concentration is 0 ppm, and at the point p18, the NO concentration is 200 ppm, the $NO_2$ concentration is 150 ppm, and the $NH_3$ concentration is 150 ppm. If there is no corresponding point on the second map 112, the point nearest thereto may be specified, and the NO concentration, the $NO_2$ concentration, and the $NH_3$ concentration may be obtained, for example, by a known type of approximation calculation.

Next, the process of measuring NO, $NO_2$, and $NH_3$ by the fourth gas sensor 10D will be described with reference to the flowcharts of FIGS. 21 and 22.

Figure 21:
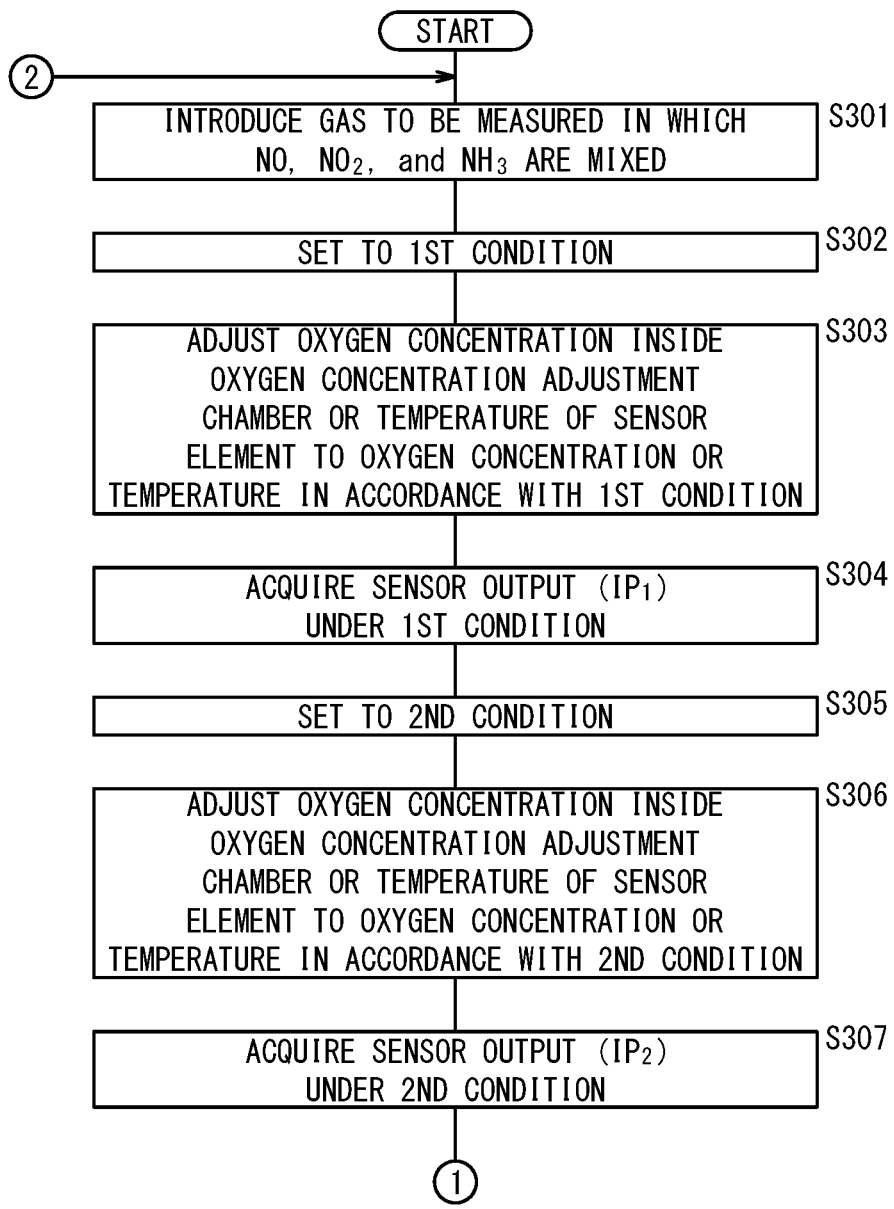
FIG. 21 is a flowchart (first part thereof) showing a process of measuring NO, $NO_2$, and $NH_3$ by the fourth gas sensor.
Figure 22:
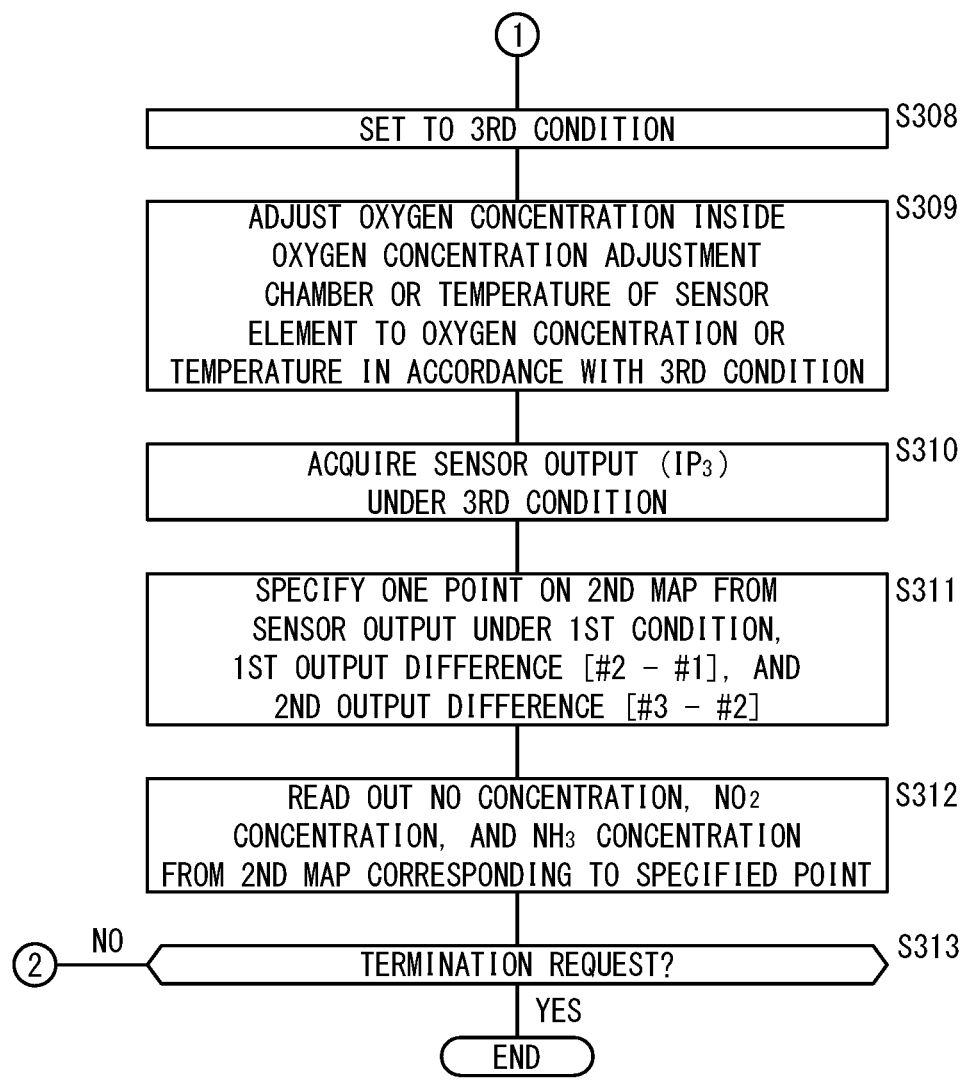
FIG. 22 is a flowchart (second part thereof) showing a process of measuring NO, $NO_2$, and $NH_3$ by the fourth gas sensor.

First, steps S301 to S310 in FIGS. 21 and 22 are the same as those of the above-described third gas sensor 10C (refer to steps S201 to S210 in FIG. 18), and therefore, duplicate descriptions of such steps will be omitted.

Thereafter, in step S311 of FIG. 22, the concentration calculation unit 106 specifies one point on the second map 112 from the sensor output under the first condition, the first output difference [#2–#1] obtained by subtracting the sensor output under the first condition from the sensor output under the second condition, and the second output difference [#3–#2] obtained by subtracting the sensor output under the second condition from the sensor output under the third condition.

In step S312, the NO concentration, the $NO_2$ concentration, and the $NH_3$ concentration corresponding to the specified point are read out from within the second map 112, and at this time, the concentrations are set as the measured NO concentration, the measured $NO_2$ concentration, and the measured $NH_3$ concentration. If there is no corresponding point on the second map 112, the point nearest thereto may be specified, and the NO concentration, the $NO_2$ concentration, and the $NH_3$ concentration may be obtained, for example, by a known type of approximation calculation.

In step S313, the fourth gas sensor 10D determines whether or not there is a termination request (power off, maintenance, etc.) to terminate the measurement process of NO, $NO_2$, and $NH_3$. If there is not a termination request, the processes from step S301 of FIG. 21 and thereafter are repeated. In addition, in step S313, at a state at which a termination request is made, the process of measuring NO, $NO_2$, and $NH_3$ in the fourth gas sensor 10D is brought to an end.

The fourth gas sensor 10D also realizes the same effects as those of the above-described third gas sensor 10C. In particular, since it is sufficient to read the NO concentration, the $NO_2$ concentration, and the $NH_3$ concentration from points specified on the second map 112, there is no need for a complicated calculation process, and the NO concentration, the $NO_2$ concentration, and the $NH_3$ concentration can be acquired in a short period of time.

The gas sensor and the method for measuring concentrations of a plurality of target components in a gas to be measured according to the present invention are not limited to the above embodiments described above, and it is a matter of course that various configurations could be adopted therein without deviating from the essence and gist of the present invention, and in particular, the following characteristic features (a) through (c).

(a) The setting conditions for the oxygen concentration and the temperature of the oxygen concentration adjustment chamber are replaced with other conditions which differ from the reference conditions in accordance with the type of target component and the number of components.

(b) By changing the conditions referred to in item (a), the chemical equilibrium of the target components (for example, NO, $NO_2$, and $NH_3$) occurring in the oxygen concentration adjustment chamber is changed to thereby intentionally change the sensor outputs obtained in the measurement chamber.

(c) The concentrations of the respective components are determined from the sensor outputs under the reference conditions, and the changed amount of the sensor outputs due to replacement of the conditions.

For example, the auxiliary adjustment chamber 18b may be omitted, and a measurement chamber 20 having the measurement electrode 62 and the fourth diffusion rate control portion 64 may be provided on an innermost side of the oxygen concentration adjustment chamber 18 which is configured with only the main adjustment chamber 18a.

Figure 23:
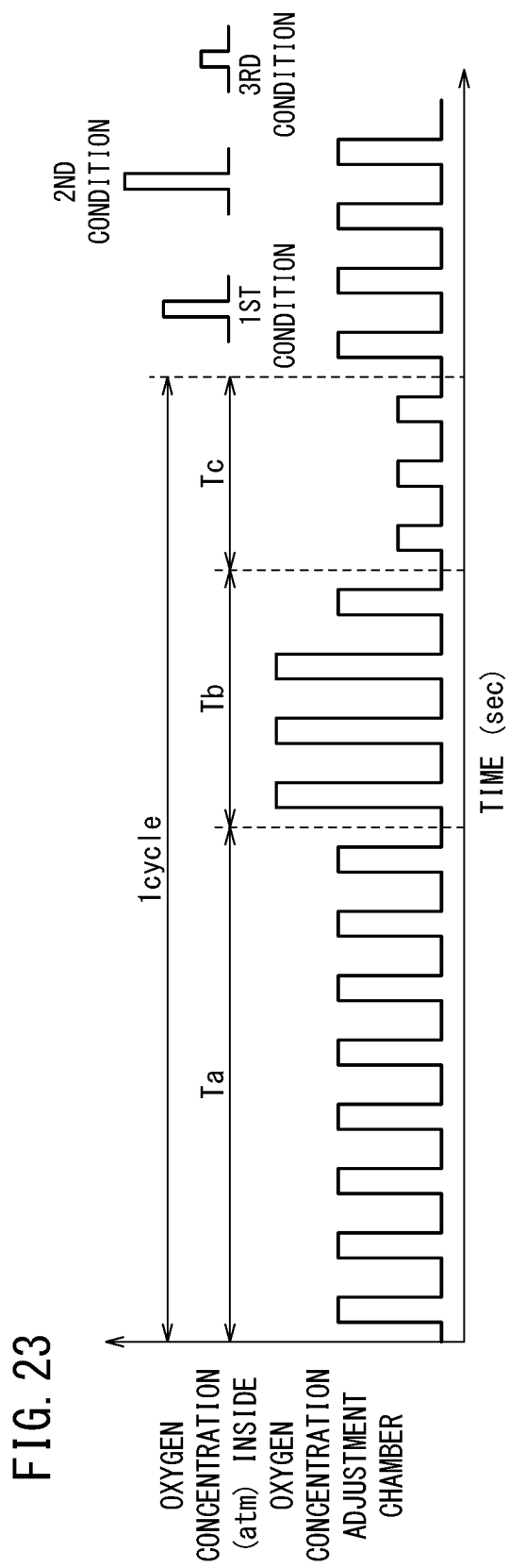
FIG. 23 is a time chart showing an example of a period that is set in the first condition, a period that is set in the second condition, and a period that is set in the third condition within one cycle.

Further, as shown in FIG. 23, the period Ta that is set as the first condition may be kept long, and the period Tb that is set for the second condition, and the period Tc that is set for the third condition may be made shorter. In this case, the sensor output under the first condition that serves as a reference can be secured with high accuracy, and the NO concentration, the $NO_2$ concentration, and the $NH_3$ concentration can be accurately measured. Further, in the process of setting the third condition from a state in which the second condition is set, the first condition may be set temporarily. It is possible to improve the measurement accuracy of the sensor output under the third condition. Of course, the period Ta that is set for the first condition, the period Tb that is set for the second condition, and the period Tc that is set for the third condition may be set respectively to equal values.

The invention claimed is:

1. A method of measuring concentrations of a plurality of target components in a gas to be measured, in which there is used a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, the method comprising:

a gas introduction step of introducing a gas to be measured;

a condition setting step of setting at least one of the oxygen concentration of the oxygen concentration adjustment chamber and the temperature of the sensor element to a condition that corresponds with at least one of a plurality of target components of the gas to be measured; and a concentration calculation step of calculating concentrations of a plurality of respective different target components, on a basis of respective sensor outputs obtained under a plurality of conditions corresponding to the plurality of target components, wherein:

in the condition setting step:
there is set, as a first condition, a condition for converting all of a first target component into a second target component, without causing decomposition of the second target component; and
there is set, as a second condition, a condition for converting a portion of the first target component into the second target component, without causing decomposition of the second target component; and
in the concentration calculation step, there are calculated the respective concentrations of the second target component and the first target component based on:
a first relational expression expressing a relationship between the concentration of the second target component, the concentration of the first target component, and an offset current which is a value of a sensor output under the first condition when the concentrations of the second target component and the first target component are 0 ppm; and
a second relational expression expressing a relationship between the concentration of the second target component, the concentration of the first target component, and an offset current which is a value of a sensor output under the second condition when the concentrations of the second target component and the first target component are 0 ppm.

2. The method of measuring concentrations of a plurality of components in a gas to be measured according to claim 1, wherein the first target component is $NO_2$ and the second target component is NO.

3. The method of measuring concentrations of a plurality of components in a gas to be measured according to claim 1, wherein, in the condition setting step, the second condition is set after having set the first condition.

4. A method of measuring concentrations of a plurality of target components in a gas to be measured, in which there is used a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, the method comprising:
a gas introduction step of introducing a gas to be measured;
a condition setting step of setting at least one of the oxygen concentration of the oxygen concentration adjustment chamber and the temperature of the sensor element to a condition that corresponds with at least one of a plurality of target components of the gas to be measured; and
a concentration calculation step of calculating concentrations of a plurality of respective different target components, on a basis of respective sensor outputs obtained under a plurality of conditions corresponding to the plurality of target components, wherein:
in the condition setting step:
there is set, as a first condition, a condition for converting all of a first target component into a second target component, without causing decomposition of the first target component; and
there is set, as a second condition, a condition for converting a portion of the first target component into the second target component, without causing decomposition of the second target component;

in the concentration calculation step, from the sensor output under the first condition, and an output difference which is obtained by subtracting a value of the sensor output under the first condition from a value of the sensor output under the second condition, there is utilized a map in which there is previously recorded a relationship between the second target component concentration and the first target component concentration respectively for each of a plurality of values specified by the sensor output under the first condition and the obtained output difference; and
in the concentration calculation step, there are determined the respective concentrations of the second target component and the first target component by comparing, with the map, the value of the sensor output under the first condition, and the output difference obtained by subtracting the value of the sensor output under the first condition from the value of the sensor output under the second condition.

5. The method of measuring concentrations of a plurality of components in a gas to be measured according to claim 4, wherein, in the condition setting step, the second condition is set after having set the first condition.

6. The method of measuring concentrations of a plurality of components in a gas to be measured according to claim 4, wherein the first target component is $NO_2$ and the second target component is NO.

7. A method of measuring concentrations of a plurality of target components in a gas to be measured, in which there is used a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, the method comprising:
a gas introduction step of introducing a gas to be measured;
a condition setting step of setting at least one of the oxygen concentration of the oxygen concentration adjustment chamber and the temperature of the sensor element to a condition that corresponds with at least one of a plurality of target components of the gas to be measured; and
a concentration calculation step of calculating concentrations of a plurality of respective different target components, on a basis of respective sensor outputs obtained under a plurality of conditions corresponding to the plurality of target components,
wherein:
in the condition setting step:
there is set, as a first condition, a condition for converting all of a first predetermined component into a second predetermined component, and for converting all of a third predetermined component into the second predetermined component, without causing decomposition of the second predetermined component;
there is set, as a second condition, a condition for converting a portion of the first predetermined component into the second predetermined component, and for converting all of the third predetermined component into the second predetermined component, without causing decomposition of the second predetermined component; and there is set, as a third condition, a condition for converting all of the first predetermined component into the second predetermined component, and for converting a portion of the third predetermined component into second predetermined component, while causing decomposition of a portion of the second predetermined component; and in the concentration calculation step, there are calculated the respective concentrations of the second predetermined component, the first predetermined component, and the third predetermined component based on:

a first relational expression expressing a relationship between the concentration of the second predetermined component, the concentration of the first predetermined component, the concentration of the third predetermined component, and an offset current which is a value of a sensor output under the first condition when the concentrations of the second predetermined component, the first predetermined component and the third predetermined component are 0 ppm;

a second relational expression expressing a relationship between the concentration of the second predetermined component, the concentration of the first predetermined component, the concentration of the third predetermined component, and an offset current which is a value of a sensor output under the second condition when the concentrations of the first, second and third predetermined components are 0 ppm; and a third relational expression expressing a relationship between the first, second and third predetermined components, and an offset current which is a value of a sensor output under the third condition when the concentrations of the first, second and third predetermined components are 0 ppm.

8. The method of measuring concentrations of a plurality of components in a gas to be measured according to claim 7, wherein the first target component is $NO_2$, the second target component is NO and the third target component is $NH_3$.

9. The method of measuring concentrations of a plurality of components in a gas to be measured according to claim 7, wherein, in the condition setting step, the second condition is set after having set the first condition, and thereafter, the third condition is set.

10. A method of measuring concentrations of a plurality of target components in a gas to be measured, in which there is used a sensor element having a structural body made up from a solid electrolyte that exhibits at least oxygen ion conductivity, a gas introduction port formed in the structural body and into which the gas to be measured is introduced, an oxygen concentration adjustment chamber formed in the structural body and communicating with the gas introduction port, and a measurement chamber formed in the structural body and communicating with the oxygen concentration adjustment chamber, the method comprising:

a gas introduction step of introducing a gas to be measured;

a condition setting step of setting at least one of the oxygen concentration of the oxygen concentration adjustment chamber and the temperature of the sensor element to a condition that corresponds with at least one of a plurality of target components of the gas to be measured; and a concentration calculation step of calculating concentrations of a plurality of respective different target components, on a basis of respective sensor outputs obtained under a plurality of conditions corresponding to the plurality of target components, wherein:

in the condition setting step:

there is set as a first condition a condition for converting all of a first target component into a second target component, and converting all of a third target component into the second target component, without causing decomposition of the second target component;

there is set as a second condition a condition for converting a portion of the first target component into the second target component, and converting all of the third target component into the second target component, without causing decomposition of the second target component; and there is set as a third condition a condition for converting the first target component into the second target component, and for converting a portion of the third target component into the second target component, while causing decomposition of a portion of the second target component; and in the concentration calculation step, from the sensor output under the first condition, a first output difference which is obtained by subtracting a value of the sensor output under the first condition from a value of the sensor output under the second condition, and a second output difference which is obtained by subtracting the value of the sensor output under the second condition from a value of the sensor output under the third condition, there is utilized a map in which there is previously recorded a relationship between the second target component concentration, the first target component concentration, and the third target component concentration respectively for each of a plurality of values specified by the sensor output under the first condition, the obtained first output difference, and the obtained second output difference; and in the concentration calculation step, there are determined the respective concentrations of the first, second and third target components by comparing, with the map, the value of the sensor output under the first condition, the first output difference obtained by subtracting the value of the sensor output under the first condition from the sensor output under the second condition, and the second output difference obtained by subtracting the value of the sensor output under the second condition from the value of the sensor output under the third condition.

11. The method of measuring concentrations of a plurality of components in a gas to be measured according to claim 10, wherein, in the condition setting step, the second condition is set after having set the first condition, and thereafter, the third condition is set.

12. The method of measuring concentrations of a plurality of components in a gas to be measured according to claim 10, wherein the first target component is $NO_2$, the second target component is NO and the third target component is $NH_3$.

* * * * *